US009877642B2

(12) United States Patent
Duret

(10) Patent No.: US 9,877,642 B2
(45) Date of Patent: Jan. 30, 2018

(54) DEVICE FOR VIEWING AN INTERIOR OF A MOUTH

(71) Applicant: Francois Duret, Fleury D'Aude (FR)

(72) Inventor: Francois Duret, Fleury D'Aude (FR)

(*) Notice: Subject to any disclaimer, the term of this patent is extended or adjusted under 35 U.S.C. 154(b) by 0 days.

(21) Appl. No.: 15/007,010

(22) Filed: Jan. 26, 2016

(65) Prior Publication Data

US 2016/0220105 A1    Aug. 4, 2016

(51) Int. Cl.
| | |
|---|---|
| *G09G 5/00* | (2006.01) |
| *A61B 1/24* | (2006.01) |
| *A61B 5/00* | (2006.01) |
| *A61B 8/00* | (2006.01) |
| *A61B 90/00* | (2016.01) |

(Continued)

(52) U.S. Cl.
CPC ............ *A61B 1/24* (2013.01); *A61B 1/00048* (2013.01); *A61B 1/04* (2013.01); *A61B 1/0684* (2013.01); *A61B 5/0088* (2013.01); *A61B 5/6803* (2013.01); *A61B 5/7425* (2013.01); *A61B 6/022* (2013.01); *A61B 6/14* (2013.01); *A61B 6/462* (2013.01); *A61B 6/463* (2013.01); *A61B 6/466* (2013.01); *A61B 6/5229* (2013.01); *A61B 8/12* (2013.01); *A61B 8/462* (2013.01); *A61B 34/20* (2016.02); *A61B 90/37* (2016.02); *A61C 1/082* (2013.01); *A61C 1/084* (2013.01); *A61C 1/088* (2013.01); *A61C 19/00* (2013.01); *G02B 27/0172* (2013.01); *G06F 3/005* (2013.01); *G06F 3/012* (2013.01); *G06F 3/16* (2013.01); *G06T 7/0012* (2013.01); *G06T 7/32* (2017.01); *G06T 19/006* (2013.01); *G10L 15/22* (2013.01); *H04N 5/2256* (2013.01); *A61B 6/145* (2013.01); *A61B 2562/17* (2017.08); *G02B 2027/014* (2013.01); *G02B 2027/0138* (2013.01); *G02B 2027/0178* (2013.01); *G06T 2207/30036* (2013.01); *G06T 2219/2004* (2013.01)

(58) Field of Classification Search
CPC ............................ A61B 1/045; A61B 1/00193
See application file for complete search history.

(56) References Cited

U.S. PATENT DOCUMENTS

| | | |
|---|---|---|
| 6,006,126 A | 12/1999 | Cosman |
| 2004/0119662 A1 | 6/2004 | Dempski |

(Continued)

OTHER PUBLICATIONS

Sielhorst, Tobias, et al.: "Advanced Medical Displays: A Literature Review of Augmented Reality;" Journal of Display Technology; IEEE, New York, US; Bd. 4; Nr.4; pp. 451-467; XP011237912; ISSN: 1551-319X; DOI: 10.1109/JDT.2008.2001575; 2008.*

*Primary Examiner* — Thomas Lett
(74) *Attorney, Agent, or Firm* — Andrew W. Chu; Craft Chu PLLC

(57) ABSTRACT

The viewing device for the interior of a mouth of a patient includes a penetrating ray emitter adapted to take a view of an inner portion located under an outer surface of an organ arranged in the mouth. There is a pair of augmented-reality glasses having an optical glass through which a user of the pair of glasses can see the interior of the mouth and a viewing camera adapted to take an image of what the user sees through the optical glass. A central unit correlates first images corresponding to those taken by the viewing camera with second images corresponding to those taken by the penetrating-ray emitter.

17 Claims, 8 Drawing Sheets

| (51) | Int. Cl. | |
|---|---|---|
| | A61B 1/00 | (2006.01) |
| | A61B 1/04 | (2006.01) |
| | A61B 1/06 | (2006.01) |
| | A61C 1/08 | (2006.01) |
| | A61C 19/00 | (2006.01) |
| | G02B 27/01 | (2006.01) |
| | G06F 3/00 | (2006.01) |
| | G06F 3/01 | (2006.01) |
| | G06F 3/16 | (2006.01) |
| | G06T 7/00 | (2017.01) |
| | G06T 19/00 | (2011.01) |
| | G10L 15/22 | (2006.01) |
| | H04N 5/225 | (2006.01) |
| | A61B 6/02 | (2006.01) |
| | A61B 6/00 | (2006.01) |
| | A61B 8/12 | (2006.01) |
| | A61B 34/20 | (2016.01) |
| | G06T 7/32 | (2017.01) |
| | A61B 6/14 | (2006.01) |

(56) References Cited

U.S. PATENT DOCUMENTS

| | | | |
|---|---|---|---|
| 2005/0206583 A1* | 9/2005 | Lemelson | A61B 1/00048 345/7 |
| 2009/0124890 A1 | 5/2009 | Derycke | |
| 2010/0149213 A1* | 6/2010 | Navab | G02B 27/017 345/633 |
| 2011/0102549 A1* | 5/2011 | Takahashi | A61C 1/084 348/46 |
| 2012/0056993 A1 | 3/2012 | Luqman et al. | |
| 2013/0242262 A1* | 9/2013 | Lewis | G02B 27/0093 351/209 |
| 2014/0378762 A1* | 12/2014 | Hirabayashi | A61B 1/045 600/109 |
| 2015/0281680 A1* | 10/2015 | Grafenberg | H04N 13/004 348/50 |
| 2016/0128624 A1* | 5/2016 | Matt | A61B 5/4542 600/301 |
| 2016/0225192 A1* | 8/2016 | Jones | G06F 3/012 |

* cited by examiner

DEVICE FOR VIEWING AN INTERIOR OF A MOUTH

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to a device for viewing the inside of a mouth, namely a device permitting to see an inner portion located under an outer surface of an organ arranged in the mouth.

2. Description of Related Art Including Information Disclosed under 37 CFR 1.97 and 37 CFR 1.98

The known devices aimed at viewing in the field of dental treatments of the invisible sub-gingival, coronary, radicular or osseous parts include the following devices:

- a penetrating ray emitter such as an X-ray device operating in 2D (conventional radiography or radiovisiography), in 2D½ or 3D (scanner, cone beam, panoramic scanner or orthopantomograph) or an MRI device, an ultrasound device, a device operating with terahertz radiation or a device operating with the techniques derived from the holographic interferometry (OCT);
- eventually an intraoral camera for taking an impression by optical means (radiation ranging from deep blue to X-ray, even ultrasound), whether using a structured projected light or not; and
- a remote display screen permitting to see, on the one hand, the view of the modeling from the device emitting penetrating rays and, on the other hand, the modeling obtained as a result of the scanning performed using the intra-oral camera displayed after the clinician has performed the optical impression.

Radiology devices used in dental treatments can be divided into two large categories, those located close to the dental unit and the remote ones.

In the first category we find devices using silver-based, phosphor-based or digital supports (radiovisiography or RVG).

Though the silver-based devices are increasingly less used, this is not the case for the other two, since they permit to scan indirectly (phosphor-based supports) or directly (RVG) the pixelated radiological image obtained from osseous tissue by transparency to X-rays. In both cases, the image obtained is scanned in grayscale and displayed in 2D on a screen near the practitioner, in black and white or in reconstructed virtual colors. This image allows him to know the sub-gingival condition of the osseous tissue, but also of the crowns and roots of the teeth.

The clinician carries over and intuitively matches the viewed shapes seen on the 2D screen onto the parts visible in the mouth of his patient. This allows him to have a very rough idea of knowing the shape and length of a root, of knowing whether there are pathological pictures and to imagine the position of the nerves and the big blood vessels. If he also wants to monitor over time whether his treatment is effective or not, he will have to make several successive pictures.

With the emergence of a more demanding dentistry, in particular addressing the treatments in periodontology and implantology, more complex devices, which represent a second category, have been used. These devices are rarely present in the dental office, but they allow the dentist to have a general view of the entire mouth in 2D, 2D½, even 3D if he uses magnetic resonance (MRI).

In this category we have found over the last thirty years the oral scanners (pantographs, panoramic scanners) providing 2D images of the entire arch in one picture, the CT scanner providing 2D½ images that permit, thanks to the different voxel planes, to reconstruct a false 3D image (scanner) and more recently the cone beams combining the advantages of the traditional scanner and the CT scanner providing a very fast and much more accurate 2D½ picture of the osseous tissue.

The latter images are widely used in implantology where the practitioner should exactly know the position of the underlying organs such as the sinuses and the various osseous structures when preparing the site for receiving his future implant.

In all cases, these spatial 2D½ (or false 3D) images are shown on a remote 2D screen permitting to move them in three planes in space and to know where the interesting areas or risk areas are located.

Finally, some practitioners use real 3D images in MRI, but this is still seldom and very expensive. In this case too, the display will occur on a remote monitor.

Recently, and in view of the inaccuracy of the radiological image, some clinicians have decided to associate with the inaccurate X-ray image (100 to 200 microns) a much more accurate (10 to 30 microns) image of the outer portion obtained using an intraoral camera for optical impression. By blending the first and the second image, they get on the remote 2D screen a combined view of the tissues and the underlying organs and the optical impression of the teeth and the gums.

Unfortunately, though the knowledge of the proximity of an underlying organ is acceptable to within about one hundred microns, this is not true for the accuracy of a crown or the cylinder of an implant, which must be known to within about ten microns.

If they use the systems described above for the sub-gingival view, they need in addition an optical impression camera in order to have a sufficiently accurate external view.

Nowadays, as a direct result of the works by the inventor François Duret, there exist different kinds of methods for taking an intraoral optical impression in the dental practice, which can be combined in a radiological image. We find:

those projecting onto the tooth a structured light, which may be a dot, a line or a complete grid. They have been widely known for several decades and are very well described in the article by G. Hausler and Col "light sectioning with large depth and high resolution" in Appl. Opt. 27 (1988). They can use, for example, projections of grids with variable pitch ("numerical stereo camera" SPIE Vol 283 3-D, 1981), the principle of the profilometric phase (Duret U.S. Pat. No. 5,092, 022 and U.S. Pat. No. 4,952,149), the best known of which is the CEREC (Sirona GmbH), the one that combines the projection of the fringe and phase variations of the Hint-Els Company (USA) or the parallel confocal principle such as the Itero (US.0109559) from Cadent (USA).

those that do not use the projection of active or structured light, but the stereoscopic interferometry. This is the case of the Lava AWS camera from 3M (Rohaly and Co, U.S. Pat. No. 7,372,642) or the Condor camera from Duret and V & O Querbes (U.S. Pat. No. 8,520, 925).

Though we can say that all these works and inventions have led to many embodiments and to more than twenty commercially available systems (F. Duret, dental floss No. 63, May 2011, "the great adventure of the CADCAM at the IDS in Cologne" 14-26), none of them has provided an original solution permitting to display the impression of the visible and invisible parts directly in the mouth during and after their taking.

All these described methods, implemented in dental offices or in another room for large radiology devices, use the same display system: a remote screen close to or far away from the operator. Irrespective of the complexity of these devices, with all the cameras or radiology devices that we have described above is associated a screen. It can be placed on a kart, be connected to or depending (all-in-one) on a computer or be part of or the whole laptop or tablet.

In the case of a data-processing monitor (video, plasma, LCD or LED). The screen is specific to the application, radiological or display of the optical impression being taken. Sometimes it combines the two methods (Planmeca, Carestream) by displaying in two different windows the video picture from the camera view and the modeled picture resulting from the radiological and/or intraoral digital processing.

On this same screen can be displayed the practitioner's interactive view that permits him to complete the information relating to the patient: the medical characteristics and the care to be brought or already brought. This is referred to as the patient card. In this case, it is no problem to display this information on a remote screen, since the elements contained in this card are rarely completed during the actions or need not be displayed during same. Although this has already led to making an augmented-reality application, for us it is of little interest to the patient's health. This is not case as regards the displaying of his physiological data during the intervention, as we will see in the accessory applications of our invention.

The digital central processing unit (CPU) collects and processes the information proceeding from the intraoral camera and the radiology devices, then displays them on the display screens.

We immediately understand that the first problem faced by the operator is to have to look on one or more remote screens at the radiological view and the one proceeding from his intraoral camera. If he uses a silver-base support, he has no option but to use a light box. This obliges him to look away and to never have any accurate match between his clinical space, which is what he sees in his patient's mouth, and the sub-gingival area, which is radiologically known and displayed on the monitor.

We understand why the clinician must constantly take his eyes away from his operating field to the remote image.

In addition, though he is provided with augmented-reality indications on the remote screen, he must not only make the effort of moving his eyes from his operating field to the monitor, but also of transposing with his brain and virtually these indications and information displayed on the remote 2D screen to the operating field, with the risk of being inaccurate or of doing it wrong.

This is extremely uncertain, especially since the only region corresponding to a common volume between the visible part and the sub-gingival part permitting a correlation by the mind is in the radiological view displayed in 2D on the screen, while in the mouth his vision is three-dimensional. The operation is so inaccurate in implantology that the clinicians must use guides, which are secured to the teeth, so that their drill bits do not injure the underlying tissue.

We easily understand that seeing indirectly the course and the result of his work is dangerous for the patient, inaccurate, incomplete and extremely damaging in daily practice. We can summarize the issues arising from this way of displaying on a remote screen as follows:

this obliges the latter to permanently move his eyes between the body part on which he is working and the remote screen. Indeed, if the practitioner wishes to follow the evolution of his endodontic or surgery work, he must move his eyes away from the body area on which he is working and watch his video or digital screen (monitor) in order to guess where his work is located, this movement can lead to adverse, inaccurate and uncontrolled movements of his hands during his work, which issue is especially important when he works for a long period (fatigue), this movement is dangerous because his eyes regularly leave the operating field at the risk of causing an injury in the patient's mouth or body or of breaking his instruments.

this is also very tiring because the existence of a remote display requires eye gymnastics at a very high pace. It is thus possible to have more than 20 to-and-fro movements of his eyes per minute.

This excludes any additional directly correlated information about the viewed field as is now possible with the augmented reality. Having no correlation between the actual view and the information proceeding for example from the augmented reality on a remote screen excludes any real time and any accurate information in the operating field. Even though this information appears on the remote screen, the display will never be in real time and the clinician's gesture will not be positioned accurately in the working field.

This action is inaccurate: we see that though it is possible to see the underlying tissues on a remote screen, the direct viewing of his work is never secure, because moving his eyes and changing the clinical action area during his work makes difficult the correlation between the two observations. There exists no real correlation between the RX representation and the working field, due to the use of the remote screen. This also applies to any information from the augmented-reality software transferred onto the remote screen.

This operation is insufficient: the RX radiation produces a 2D or 2D½ display transferred onto a 2D screen, which makes it especially difficult, even impossible, to estimate what has been x-rayed with respect to what is actually present in front of the operator in 3D eye vision.

This medical procedure is not secure: we can say that no simple and especially secure solution has been found to meet the needs of the clinician. For his action to be secure, he must see the area that has been X-rayed and the area on which he is working combined in real time in one and the same repository. This is the essential condition for being able to work safely, quickly, with total comfort and with the accuracy required for this type of intervention.

BRIEF SUMMARY OF THE INVENTION

The present invention aims at coping with these aforementioned drawbacks by providing a new viewing device.

The invention relates to a device for viewing the inside of a patient's mouth, the viewing device comprising a penetrating ray emitter adapted to take a picture of an inner portion located under an outer surface of an organ arranged in the mouth, wherein it comprises a pair of augmented-reality glasses having, on the one hand, an optical glass through which a user of the pair of glasses can see the inside of the mouth, and, on the other hand, a viewing camera adapted for taking an image of what the user sees through the optical glass, a central unit being adapted to correlate first images corresponding to those taken by the viewing camera with second images corresponding to those taken by the viewing camera with second images corresponding to those taken by the penetrating ray emitter.

According to a first embodiment, the central unit is adapted to orient the second images depending on the orientation of the pair of augmented-reality glasses.

According to a second embodiment, the central unit is adapted to project onto the optical glass the correlation of the first images with the second images.

According to a peculiarity of the second embodiment, the central unit is adapted to project onto the optical glass, at request by the user, images from a selection of anatomical components of the organ taken by the penetrating ray emitter.

According to a third embodiment, the viewing device includes a medical treatment instrument comprising, on the one hand, a tool that is adapted to process anatomical components of an organ, which it is into contact with, and, on the other hand, a reference mark, which is adapted to be spatially identified during the processing of the anatomical components, and wherein the central unit is adapted to know the dimensions of the tool and the distance separating the tool from the reference mark, and to determine the position of the tool in the organ during the treatment.

According to a first peculiarity of the third embodiment, the central unit is adapted to make third images that represent the tool used for the treatment, to correlate them with the second images, and to project the correlation so as to permit viewing the tool in the organ being treated.

According to a second peculiarity of the third embodiment, since the length of displacement of the tool is equal to the length of displacement of the reference mark, the central unit is adapted to determine the direction and the direction of movement of the tool relative to the anatomical components, which it is into contact with, the direction and the direction of movement of the tool being either equal to the direction and the direction of movement of the reference mark, when the tool is not deformable relative to these anatomical components, or determined by the relief of these anatomical components, when the tool is deformable relative to the latter.

According to a third peculiarity of the third embodiment, the central unit is adapted to determine the ideal movement of the tool used to carry out a treatment. According to an advantageous embodiment of the third peculiarity of the third embodiment, the central unit is adapted to guide the user for the tool being used to follow the ideal movement.

According to a first preferred embodiment of the advantageous embodiment of the third peculiarity of the third embodiment, the guidance of the user is carried out by displaying the ideal movement on the optical glass correlated with the second images.

According to a second preferred embodiment of the advantageous embodiment of the third peculiarity of the third embodiment, the guiding of the user is carried out by emitting a sound signal depending on the position of the tool being used.

According to a fourth peculiarity of the third embodiment, the tool being used is identified by an identifier and in that the central unit is adapted to receive the identifier and to determine the corresponding tool.

According to an advantageous embodiment of the fourth peculiarity of the third embodiment, the central unit comprises a library of identifiers, each identifier corresponding to a tool that is part of the viewing device.

According to a fourth embodiment, the viewing device comprises a camera for taking an optical impression adapted to take an optical impression of an outer surface of an organ arranged in the mouth, the central unit being adapted to correlate fourth images corresponding to those taken by the camera for taking an optical impression with the first images.

According to a fifth embodiment, the correlation of the images performed by the central unit is a superposition and/or a replacement of the images on the optical glass.

According to a sixth embodiment, the central unit is adapted, at request by the user, to change the contrast and the transparency of the images it processes.

According to a seventh embodiment, the penetrating ray emitter is adapted to transmit digitally to the central unit the images it takes.

According to an eighth embodiment, the viewing device comprises a scanning device adapted to scan the non-digital images emitted by the penetrating ray emitter and to transmit the scanned images to the central unit.

According to a ninth embodiment, the central unit is adapted to project onto the optical glass additional information relating to the patient.

According to a first peculiarity of the ninth embodiment, the additional information relating to the patient comprises data to be respected for making a dental prosthesis.

According to a second peculiarity of the ninth embodiment, the viewing device comprises at least one peripheral instrument connected to the central unit and adapted to capture additional information relating to the patient.

According to an advantageous embodiment of the second peculiarity of the ninth embodiment, one of the peripheral instruments permits either to capture the static occlusion and jaw movements or to capture the color of teeth, or to capture the shape of the face, or to capture of the patient's physiological data.

According to a tenth embodiment, the viewing device comprises a microphone adapted to capture control commands proceeding from the user and to transmit them to the central unit.

According to an eleventh embodiment, the pair of augmented-reality glasses comprises a spatial marking instrument.

According to a twelfth embodiment, the viewing device comprises a lighting system adapted to illuminate the organ arranged in the mouth.

According to a peculiarity of the twelfth embodiment, the lighting system comprises light-emitting diodes the wavelength of which is adapted to permit the identification of diseases.

According to a thirteenth embodiment, the central unit is adapted to project on a remote screen images relating to the organ arranged in the mouth.

According to a fourteenth embodiment, the central unit is adapted to control a numerical-control machine for making a prosthesis relating to the organ arranged in the mouth.

Thus, the device according to the invention combines in one and the same field, perfectly correlated or very close, the direct viewing through augmented-reality glasses of the operating area the practitioner sees in the mouth or on the face of the patient through his glasses, the modeling obtained by radiography (RX, ultrasound, MRI or holographic interferometry—OCT), eventually supplemented with the modeling proceeding from the processing resulting from the reading of the optical impression of a very accurate intraoral camera and all the additional information that may help the surgical procedure, which is in turn correlated in the same repository.

By additional information, we understand, and this is just one example, the path followed by a canal-treatment, a surgical treatment instrument or by drill bits normally invisible in implantology when we do not use X-rays. This point is extremely important, because it should permit to follow, without increasing the exposures to RX, real-time procedures in the mouth without these being visible through normal glasses.

This invention thus fully solves the problems set forth by providing an adaptable inexpensive solution usable in all dental practices in a simplified and patient friendly form.

In particular, it solves the many above-mentioned problems:

- thanks to this new and original organization the practitioner can see through his augmented-reality glasses, in the same field, i.e. in the mouth of his patient, (a) the body part he is analyzing and on which he is working, (b) the sub-gingival and osseous view obtained from the radiology, ultrasound, MRI or holographic interferometry (OCT . . . ) devices, (c) eventually, if he wants accuracy, the modeling he obtains by optical impression with his three-dimensional reading intraoral camera, the three views being totally combined without using the remote screen. Indeed, if the practitioner wants to monitor the evolution of his surgery (implants, extractions . . . ) or endodontics work, he will see through superimposition or any other form viewable as a change in intensity, color or contrast, and this is given only as an example, the supra-gingival surface (teeth and gums . . . ) and the sub-gingival part (bones, nerves, vessels, sinus . . . ) without moving his eyes away from the body area on which he is working and is making his diagnosis. He can therefore monitor in real time or with delay the environment and the result of his supra- and sub-gingival action without taking his eyes away from his operating field.
- thanks to the matching of this information, he is no longer likely to make harmful and uncontrolled moves of his hands during his work, which advantage is especially important if he wants to permanently monitor his actions in areas inaccessible for the eyes, without using penetrating radiations (RX . . . ).
- thanks to the elimination of the taking away his eyes from his operating field he will no longer risk causing an injury in the mouth or on the body of his patient, because his actions and the information attached to the result of his action or helping him to achieve them will permanently be visible in his working area.
- by choosing to make a correlation between the actual view and the sub-gingival and osseous invisible view after processing the information, it is possible to use any kind of method for taking an accurate optical impression, irrespective of it being or not an impression resulting from a method using a structured active light. It is also possible to use any kind of penetrating radiation like X-rays, ultrasound, MRI or holographic interferometry (OCT . . . ). This method of superimposition and/or augmented-reality substitution is fully independent from the type of reading being adopted, as is the additional information from the augmented reality.
- by using a central unit, he will be able to store the follow-up of all these actions, which is very important during examinations (implantology, temporal or post-operative semiotics . . . ).
- due to the absence of any eye movements likely to involve strong eye gymnastics at a very high pace, the operation will become very relaxing for the clinician.
- thanks to the use of glasses having the possibility of displaying an augmented reality it will be possible to provide information in real time or with delay, at the discretion of the clinician, in the operating field. This includes any directly related additional information on the viewed field, like the augmented reality nowadays permits, but also information from additional information sources like that from telemedicine.
- thanks to the optional additional information from the augmented reality, it also permits:
  - to guide the operator on the site by telemedicine, but also by a personalized expert or learning system when important areas are not treated properly.
  - to show specifically and on site sub-gingival information from a fragile or important environment.
  - to warn the clinician during the surgical procedure when it is not performed perfectly. It is possible, for example, to indicate incomplete root canal treatments, drilling of insufficiently or incorrectly positioned implant cylinders, incomplete extractions or curettage.
  - to reveal and to permit to view on site the dynamic movements of the instruments being used or parts of the body being treated during the performing of difficult extractions, the fitting of implants or the drilling of root canals.
  - to highlight in the mouth the distribution of the dental tissues, for example the proximity of the pulp, during the preparation of cavities for receiving a filling and a crown.
  - to follow in the mouth and in real time the path followed by any instrument the clinician uses, in order to increase his efficiency and to avoid accidents on the environment (veins, nerves . . . ).
- thanks to the means being implemented, the device is simple to be manufactured, which makes it particularly strong. It also permits:

to significantly reduce the manufacturing cost, hence the sales price since the democratization of the electronic elements being used, such as the new generation Condor cameras, the virtual-reality glasses or the LEDs.

to choose a wired or a wireless connection, including at the level of the camera, which permits fully free movements of the clinician.

to have the stereoscopic natural 3D restitution without being obliged to use 3D screens, which are always expensive and often inefficient.

Further aims and advantages of the present invention will become clear from the following description relating to an embodiment given by way of an indicative and non-restrictive example. The understanding of this description will be facilitated when referring to the attached drawings.

DETAILED DESCRIPTION OF THE INVENTION

Figure 1:
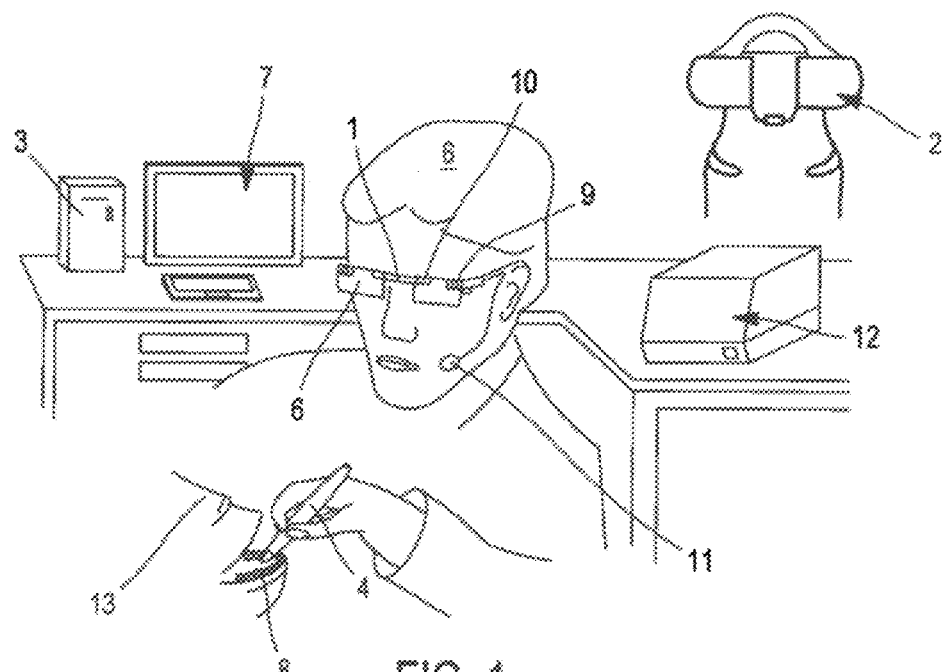
FIG. 1 is a schematic view of a representation of the whole of the device comprising all the main elements necessary for its proper operation, but also the additional peripheral, but not compulsory elements.

The present invention relates to a novel device in the dental field for intraoral viewing and/or measuring directly on the working site, i.e. in the patient's mouth, bringing together in one and the same three-dimensional or slightly shifted repository (a) the direct view of the teeth and gums in the patient's mouth through the augmented-reality glasses, (b) one or more modelings from taking radiological impressions—OCT and/or MRI, (c) one or more references or modelings from the cameras present on the augmented-reality glasses through which the practitioner views the patient's mouth, (d) eventually one or more references or modeling from an optical impression using structured light or not made using an intraoral camera, so that they complement and/or replace each other in order to enrich themselves using the principle of the augmented reality, and (e) eventually additional information associated herewith and provided by other peripheral devices, in order to permit the clinician to never take his eyes away from his intraoral working site, namely during gingival, coronary, root canal, surgical or bone treatment, in order to secure, facilitate and optimize his clinical action, this application being however non-restrictive in that the device is also applicable in the follow-up of all the clinical activities of the dental office.

To this end, this device according to the invention permits to view directly in the patient's mouth, through augmented-reality glasses, and in a way perfectly correlated, both the visible and the invisible part of the mouth in the form of one single object, which is here referred to as the complemented object.

The visible part is the surface of the teeth and the gums, the tongue and inner side of the cheeks. It can be seen directly through the glasses, but it can also be seen in the form of a scanned view resulting from the reading of a stereo-dynamic camera, or of several cameras located on the glasses or, more accurately, thanks to the digitized picture obtained by the scanning performed using the intraoral camera. The scanning can be substituted, without this being compulsory, by a direct vision in the scanned parts from the less accurate to the more accurate one, i.e. in the order of the most accurate domination (the intraoral camera) replaces the less accurate (camera of the glasses), which can in turn be substituted by the non-digitized direct view.

The invisible part results from a reading made separately before the therapeutic action through peripheral devices capable of providing RX, MRI, terahertz or ultrasonic images of the invisible parts located under the teeth, under the gums or under the skin, as are the bone, the epithelial and conjunctive tissues, the blood vessels and the nerves. These devices permit to statically or dynamically know, store and scan the invisible underlying anatomy.

For these two volume units, the visible and invisible part then forms one single unit, the central unit seeks the common parts and combines the two objects based on these common parts. These common parts can be anatomical objects, such as the crowns of the teeth or applied objects such as the locating wedges fixed in the mouth, for example on the teeth, if one wishes to avoid any abnormal mobility. These wedges or these anatomical reference marks are also used as an identification for following up the movement of the instruments made for this purpose.

Preferably and in some cases, it is possible to scan simultaneously invisible and visible parts. This is the case if we use an ultrasonic or terahertz device.

To this end, the invention is comprised of 1) a viewing device operating in real time or with a delay using augmented-reality glasses, which a three-dimensional spatial locating system (at least accelerometers/gyroscope and cameras) can be associated to and the function of which is to permit the practitioner not only to see his operating field in direct vision, but also to have punctual indications or external views, as all the glasses of this kind permit for assisting surgery, which permits him to normally follow the normally visible progression of his work (for example root canal treatment or surgical actions), i.e. the external part of the teeth and gums. It also permits him to add in addition correlated images, and this is the essential feature of the invention, resulting from 2) a second peripheral device. This second peripheral device is capable of providing RX, MRI, or terahertz ultrasonic images of the invisible parts that are located under the teeth and under the gums, such as the bone, the epithelial and conjunctive tissues, the blood vessels and the nerves, and to permit to know, store and scan the invisible underlying anatomy. The two devices 1) and 2) are dependent 3) on a central unit the function of which is to scan the views from the cameras located on the glasses and on the peripheral device in order to correlate them to combine them in one and the same repository, so that the clinician sees in the mouth of his patient, through his augmented-reality glasses, one single object from the combination of the view he naturally gets through his augmented-reality glasses, with which is combined permanently, dynamically and in real or almost real time, the various information from both external elements, the teeth and the gums, but also of the invisible elements, which permits the latter to have in its field of view in the mouth his patient the visible part, but also the invisible part located under the gums and under the teeth.

This thus permits the user to follow his action without taking his eyes away and to know the consequence of his action in a portion normally inaccessible to his eyes in the mouth. It should be noted that the present device, in order to avoid a permanent irradiation of the patient, needs only at least an initial 3D image and that he will correlate it in real time or almost real time depending on the viewing field, varying depending on the direction of the eyes of the practitioner, the cameras on augmented-reality glasses are filming.

To this device will preferably be added 4) an intraoral camera for taking an accurate optical impression using coherent radiation or not, with or without projection of active/or structured light the function of which is to perform a very accurate record of the shapes and colors of the anatomy present in the visible part of the patient's mouth, such as his teeth and/or his gums, this taking of an impression being correlated and combined by the central unit 3) with the previous views and more particularly with the less accurate view from the cameras carried by the augmented-reality glasses 1), but also and therefore with the sub-epithelial images from the external peripheral device 2). This permits the clinician to have in his working field an extremely accurate view of the portion resulting from the augmented-reality treatment.

Eventually and preferably, there will be added 5) a lighting system on the intraoral camera or on the glasses, the function of which is to optimize the diagnostic analysis such as for example the highlighting by special radiation of the carious areas on the hard tissues or tumors on the soft tissues.

In order to follow the movements in endodontics or surgery, it is enough to correlate the displayed instruments, known or calibrated on the double view—visible and invisible.

This process permits to optimize the therapeutic action of the clinician by significantly increasing the safety necessary for his actions while ensuring the structural integrity of the human body and providing accuracy within one micron. It permits especially to completely release the practitioner from determined constraints obliging him to watch a remote screen, to correlate different images of the visible and invisible area and to stay close to his working unit.

The invention comprises a hardware device and a software system.

The hardware device associates 1) a system for direct dental viewing of the visible tissues associated with the specific and miniaturized augmented reality, 2) a system for scanning the underlying tissues invisible to the naked eye, 3) a central unit for analog/digital conversion, management and correlation of the data, 4) eventually an accurate intraoral three-dimensional reading camera with or without structured light, 5) eventually an intraoral illumination specific for diagnosis, and 6) calibrated and known instruments used in the visible and invisible fields.

To this end, the object of the present invention is a device comprising specifically a viewing/capturing system with augmented-reality glasses, a device permitting to scan the parts invisible to the naked eye, a central unit, an intraoral accurate scanning camera, a lighting system and auxiliary devices.

The display/capturing system with augmented-reality glasses 1 permits to see the area of therapeutic action in direct viewing, while being able to correlate with same, then to add to same, when they have common connecting areas, additional information invisible to the eye directly from independent peripheral devices such as the images from the RX, MRI, terahertz or ultrasonic reading systems.

This viewing, displaying and capturing system may consist, for example, and this is only a non-restrictive example for the invention, of "Google Glass", "Vuzix Smart Glass", "Sony", "K-Glass" or "HoloLens" glasses.

To these glasses are added one or more cameras permitting to readjust permanently and in real time by successive tracking the modeling resulting from the reading of the sub-gingival peripheral devices using common markers such as, and this is only an example, the crowns of the teeth or markers voluntarily placed on their surfaces or on the gum on what the clinician sees in the patient's mouth.

Eventually, advantageously according to an additional feature of the device according to the invention, for financial reasons, the device can be based on a 2D viewing, the essential function of the glasses is to show additional information with inaccurate adjustment on the working area in relief. The central unit is nowadays capable of correlating the 2D views on a 3D pattern.

It can also create a 3D image using two or more 2D radiologic images by applying equations that are now well known.

In the case of a 2D½ or 3D viewing, i.e. since these glasses have spatial vision, generally using stereoscopy, without this being systematic, the correlation is very accurate and the indications occur on parts of the body read in 3 dimensions. This is made possible by the presence of dedicated specific screens existing on this kind of glasses.

Advantageously and according to an additional feature of the device according to the invention, the presence of a mini-USB mini-micro on the arm (right arm in the case of Google glass) permits to give orders for viewing and showing augmented-reality information without the operator having to move his eyes from his working area.

The device permitting to scan the parts invisible to the eye 2 can be an analogue (then passing through a scanning tablet) or a 2D or 2D½ digital radiology system for example, and this is not a limitation of the invention, such as a RVG scanner or tomography. It can also use penetrating coherent optical systems, such as for example the OCT. It can also use the 3D imaging principles of MRI or beta cameras. Very recently appeared the terahertz imaging. This has the disadvantage of still being inaccurate, but has a big advantage of using a non-ionizing vector. It can be used as a peripheral device, part of the invention. This also applies to all ultrasonic systems, irrespective of their type.

The aim of this second specific component of the invention is to collect the information invisible to the eye, in order to create a second object permitting to complement the object created during the viewing of the visible parts.

The central unit 3 permits the conversion of the analog/digital data and the management of these data. The advantage of this system is to scan the data proceeding from the cameras located on the glasses, to scan and/or to collect the images proceeding from the peripheral devices (RX, MRI, OCT, ultrasonic devices . . . ), then to combine them in order to obtain one single cloud of dots in order to form one single object. In addition to this combination, advantageously and according to an additional feature of the device according to the invention, the central unit directs the invisible part depending on the orientation of the clinician's eyes, this indication being provided by the cameras, via the reference mark, and/or the additional systems such as the gyroscopes or other devices permitting to know the positioning of an object, here the augmented-reality glasses, in space.

Thanks to this application of our invention, the central unit can follow the variation of the spatial position of the eyes, which will permit to not only see the invisible part, but also to the view it directly in the patient's mouth according to different viewing angles. This feature is important, because clinically determined anatomical structures can mask important areas. The practitioner, by shifting his eyes, will be able to see what was hidden in the previous viewing angle.

Advantageously and according to an additional feature of the device according to the invention, the central unit can show preferably the vessels, the nerves, the bone, the roots, because the current software is able to automatically detect these anatomical structures and display them in different colors.

This distinction enables the practitioner to know his working field, to select it, but also to adapt to the anatomy specific to the patient being treated. The invention permits to switch from the standard anatomy to the customized anatomy, which is particularly important in implantology or in dental surgery.

The dentist thus seen in his patient's mouth the teeth, the gums, but also all the underlying structures such as the roots of the teeth, the blood vessels, the nerves . . . , according to all the angles and selectively, eventually with specific colors.

The intraoral accurate scanning camera 4 permits to scan one or more teeth by optical impression using photonic, whether or not consistent, or ultrasonic radiation. The invention can use all the cameras used in the dental and medical world, which shows the openness and universality of the invention.

This camera can perform its metric recordings using structured-light projections. In this case, the camera possesses two or more than two combined or separate channels, one for projecting and the other one for picking up the image. A LED, OLED, halogen, plasma or laser structured-light system projects onto the teeth a radiation in the form of dots, lines or known and structured frames. This structured projection is deformed depending on the surfaces onto which it strikes, and this deformation is transmitted to a sensor through the image pickup path. This permits the camera, by comparison between the characteristics of the projected or stored light and the light deformed in space and/or over time, which arrives at the sensor, to know the shape and dimensions of the teeth being analyzed. There exist numerous intraoral cameras that meet these characteristics.

Advantageously and according to an additional feature of the device according to the invention, this camera may use any system for measuring and analyzing the shapes of the teeth and/or gums without projecting structured light. To this end, it may use single- or multi-camera telemetric or stereoscopic methods. This system has the advantage of being easier to be designed, but requires developing more complex software such as those developed for space. We find some intraoral cameras, for example and this is only a non-restrictive example, the one we have developed as the Condor camera.

Advantageously and according to an additional feature of the device according to the invention, it may also comprise cameras associating the two technologies or other principles such as the OCT, the ultrasound or the X-rays, since these provide metric information on the area and the body being examined.

It is of course possible to use natural light, but since the function of this kind of camera is to operate in dark or areas difficult to be accessed (e.g. the mouth), it is possible to have a lighting system 5 permitting a well-sized illumination of the working area.

Advantageously and according to an additional feature of the device according to the invention, the lighting system can show information on the objects being measured in augmented reality and in 3 dimensions depending on the type of lighting being used. Indeed, according to the choice of determined wavelengths, it is possible to determine and/or to find determined anatomical and pathological elements of the oral-facial sphere invisible or little visible to the eye and to show them in the operating field, in the form of augmented-reality information, unlike the direct viewings in 2D on a remote video screen. This permits the diagnosis, but also some wedging elements permitting the correlation between the image of the visible part and the underlying part, in order to build the complemented object.

The auxiliary peripheral devices can be:
  a source of information 6 proceeding directly from the stored functions or from intra- or extramural software (telemedicine) providing additional information permitting to assist the medical procedure of taking an impression and during the preparation.
  one or several peripheral stations 7, where is visible the information, which the clinician works with and which can be seen by his assistants, so that they can follow and enrich in real time or with delay (assistance or teaching . . . ). This treatment may be video and/or digital treatment.
  intraoral instruments calibrated and correlated with the image of the visible and invisible part permit to follow the real-time movements in the invisible part.
  A machine-tool with numerical control 8 that can, at any time, make a real part from the captured virtual image, so that this device finds its full application in the dental CFAO chain invented in 1970 by Francois Duret, co-inventor of this patent.

Associated advantageously and according to an additional feature of the device according to the invention, for transmitting the data from the device or its peripheral devices, are:
  a cable, telephone, Bluetooth or WiFi transmission of all data.
  an additional hardware system for processing, dialogue/viewing with the operator, the assistants and/or the central unit, for transmission and storage of the information, the orders and the data as permitted by the microphone of the display system or another form of communication.

In accordance with this hardware mounting is provided a software method that meets the requirements of quickness and accuracy necessary for the specialist in dentistry and permitting to significantly facilitate his surgical procedure.

The original software system comprises:
a real-time 3D reconstruction scheme from 2 streams of 2D images proceeding from two or more cameras of the augmented-reality viewing system;
a real-time 3D reconstruction scheme from a stream of 2D, 2D½ or 3D images proceeding from one single Rx and other peripheral device capable of viewing the elements invisible to the eye;
an algorithm for searching points of interest on the three algorithms for searching an optical trace (projection on several different cameras of the same 3D point) by calculating points of interest and matching through images;
an algorithm for automatic sequencing in real-time of the stream of images into spatially coherent subsequences permitting to follow the movement of the clinician's eyes;
an algorithm for estimation in parallel of the positions of the cameras in space and the coordinates of the 3D points thanks to the optical traces;
an algorithm for 3D interpolation of clouds of points;
an algorithm for polygonization of clouds of 3D points and texture calculation;
an algorithm for scaling the 3D reconstructions;
two algorithms for enhancing the spatial accuracy;
two algorithms for selecting the anatomical elements taking into account, among other things, the changes in contrast and density;
an algorithm for displaying the complemented object enriched with the selections of display of the anatomical elements in the complemented object; and
algorithms for correlation of the dynamic movements of instruments known to and used by the practitioner.

The overall organization of the algorithm is as follows:
The stream of images proceeding from the camera or cameras is processed in real time in order to produce a first 3D reconstruction viewable by the user as he moves his eyes about the object. The overall scheme of 3D reconstruction in real time and organization of the data vary depending on the availability of two (or more) cameras of the augmented-reality system 1 and the peripheral device 2 capturing the invisible information with delay.

Each newly acquired image is first processed by the algorithm for searching an optical trace. Based on the correspondences, the sequencing algorithm then updates the sequencing of the video stream for a better temporal performance. The parallel estimation algorithm then permits, thanks to the optical traces 1 of the peripheral devices 2 (RX, ultrasonic, MRI . . . ) a) to find the camera positions in space at the time of acquisition and b) to generate the cloud of 3D point projecting on the optical traces of the cameras on the glasses and the peripheral devices.

The single cloud of points generated is then interpolated (algorithm) in order to obtain a denser cloud, and an implicit interpolation function is calculated. Thanks to this function, a textured polygonization of the surface to be reconstructed (algorithm) is obtained. At this step, it is also possible to compute quality indexes of the final cloud of points. Determined points (or determined areas) can thus be labeled as invalid or as particular (bone, blood vessels, bone, roots . . . ).

The textured surface is finally displayed on the screen on the augmented-reality glasses, in correspondence with the direct view, eventually with appropriate annotations for indicating the still particular areas selected a priori by the clinician.

The surface generated in real time is a representation without spatial dimension representing, to within a scale factor, the reconstructed area. This scale factor can be calculated by the algorithm by hidden computation in almost real time or in real time or with a delay when the acquisition is completed.

Finally, the final 3D model can have its accuracy enhanced by the algorithm, so as to have the most accurate reconstruction possible. This algorithm recalculates a cloud of 3D points, taking into account all the views being acquired. This cloud is then interpolated by the algorithm. Finally, a space carving algorithm reconstructs the displayed global 3D model.

We also know that the radiological images are generally carrying information in clouds of 3D points carried over onto elementary units, the voxels, which can be directly correlated to the cloud of points obtained at the level of the accurate view made by the intraoral camera. On the other hand, it is impossible to combine the radiological views directly in the mouth with the views of optical impressions. The operator must follow on a remote screen the subcutaneous anatomic environment in which he works and intellectually carry over this view in the space of his operating field. This very often leads to assessment errors, especially if we admit the deflection phenomenon, i.e. that an inaccuracy of some degrees on an axis of insertion of an implant or prosthesis, a file for drilling dental canals or a trocar in medicine will result into an error of several millimeters to one centimeter of depth in the bone. The risk of injury to an organ of the human body, such as nerves, arteries and veins is therefore important.

Advantageously and according to an additional feature of the device according to the invention, it is possible to make a triple combination performed at the level of the central unit 3: the one of the accurate optical impression obtained using the intraoral camera 4, the one obtained at the level of the radiological analysis 2, whether in 2D, 2D½ or 3D, and the one observed by the cameras, through the augmented-reality glasses, although less accurate, but serving as a support for the previous two.

Therefore, the device according to the invention permits the clinician to see, without having to take his eyes away, not only an accurate surface modeling, like any known system for taking an optical impression, but in addition, a modeling of what is invisible in his operating field, i.e. the sub-epithelial and osseous part, combined with the external portion. Therefore, he has in front one single operating field where are visible the external parts and the normally invisible internal parts.

Advantageously and according to the invention, it is possible to follow the movements of the dental surgery instruments both in the roots (endodontics) and in the bone (surgery and implantology), ensuring a control of actions so far impossible in real time.

Thus, it is possible to perform root or bone scans and treatments by following the movement of the working instrument in the invisible parts, since the latter was calibrated in the repository of the taking of an optical and/or radiological impression. The practitioner sees through his augmented-reality glasses the outside of the crown, carried over by the visible, even accurate view 4 combined with the general view and through the glasses 1 and increased from the invisible view of the root (length and shape) proceeding directly from the peripheral RX, MRI or tetrahertz camera device 2, but also, which is fundamental, advantageous, and according to an additional feature of the device according to the invention, the movement of his working instruments inside this root or the bone (in surgery and implantology).

The figures represent different implementations of the device showing all the possibilities it provides in the daily practice of the dental surgeon: the augmented-reality glasses and the inaccurate viewing cameras 1, the peripheral devices viewing the invisible parts 2, the central unit 3 scanning and correlating the two visible and invisible views, the very accurate intraoral camera for the visible views 4, and the specific lighting 5.

FIG. 1 is a representation of the invention, in the form of a didactic drawing, showing the essential and auxiliary elements that can be implemented in this enriched viewing device that combines into one single view the visible and invisible parts, thanks to the augmented-reality method, and permitting the operator to never take his eyes away from his operating field when he carries out his measurements and/or diagnosis and/or his clinical actions, which device finds a particular interest in the areas of dentistry.

The device comprises augmented-reality glasses 1, such as for example Google glass, but this is not restrictive, since there are other glasses of this type, the practitioner 6 has a stereoscopic natural vision of the mouth, visible on the screen 7, thus of the area he measures and examines 8. When the operator looks at this working area, the stereoscopic camera or cameras 9 being part of the glasses, observe the same scene and are capable of performing a survey of information leading to the creation of a so-called viewing cloud of points. Since the dentist's head can move relative to the observed area, there have been added 3D accelerometer/gyroscope/magnetometer 10 close to the eyes, facilitating the following in space of the clinician's observation axis. This is not compulsory, because the software can use the connecting areas, but greatly facilitates the work of the central unit, which performs the dynamical correlation of the visible and invisible part (hereinafter referred to as complemented part) when the observer must move his eyes outside the working area, and turn back to same to continue his work.

This dynamic correlation results into the fact that, irrespective of the viewing angle, the clinician sees both parts according to different angles, which can be fundamental when, in the invisible part, an anatomical structure, for example a tooth root, hides a pathology or an area to be worked.

The invisible file of the mouth is provided by the peripheral imaging system 2. This may be a scanner or tomography systems providing, by assembling their segments, a ½ 2D view showing preferably osseous structures. In order to have a more complete view, very powerful software were added, which permits to distinguish the soft tissue in radiological images with few deformations. This was necessary in implantology where the procedure must be accurate if we do not want to risk injuring an anatomical element such as the nerves or the blood vessels. The cone beam falls within this category, it is increasingly often used, because it provides sufficient indications about the invisible hard tissues and the soft tissues, without deforming too much the 2D½ view provided after the reconstruction software. It is possible to have more accurate information directly in 3D in the implementation of the present invention by using a more complex and more expensive imaging technique, such as the MRI or the beta-cameras. Finally, yet as a peripheral device 2 of the present invention, more recent techniques such as OCT (coherent tomography optics) or imaging by terahertz can be implemented, which have the advantage of not being, in common with the MRI, ionizing. Finally, there is the ultrasound imaging, which can permit to view the underlying tissues in real time, as described in Patent FR 83.07840 of May 4, 1983 "method for capturing the shape of human organs or pathological anomalies and device for its implementation". Even though it cannot be excluded from the present invention, the problem of the ultrasound remains its inaccuracy.

In all cases, the current peripheral devices 2 permit to scan the invisible part of the mouth and to separate the different anatomical components in order to let them appear or disappear specifically, because these techniques can nowadays distinguish the vein from the artery, the nerves from the blood vessels, the roots (very dense) from the bone and the root canal from the rest of the root. This will be very important in clinical manipulation, specific to this invention, which we will describe later.

The third part of the present device is the central unit 3 in charge of managing the digital information from the surface of the visible parts transmitted by the cameras of the augmented-reality glasses and those invisible parts transmitted in real time (e.g. ultrasound) or with delay (e.g. cone beam). In particular, it will have to find the common areas permitting to correlate the two clouds of points leading to the construction of one single complemented object (combining the visible and invisible parts into one single cloud of points). This is to carry over at any time the invisible view onto the visible view the clinician observes relying on common elements. It is also to make this invisible part dominant over the visible part with an adjustable transparency index.

The present invention includes accessorily a camera for taking an optical impression 4 permitting the dentist 6 or doctor to perform his 3D measurements in the mouth or on the skin of his patient with high accuracy. Since this measurement is very accurate (to within a few microns) and very close to the teeth, the field depth is very small, which is why he must proceed to a scanning of all the teeth 8, by successive picture (one shoot impression) or by 3D filming (full motion).

In this case, the two measurements, the one obtained with the intraoral camera 4 and the one obtained with the cameras of the glasses with augmented reality 1, provide two files corresponding to the same area, but which have not the same accuracy. These files can be simple electro-optical information or more sophisticated information, such as digital representations in the form of clouds of points or even surface or volume modelings. In all cases, common values exist in these two files, which are also used to obtain the complemented object, such as for example the points located in easily identifiable areas, such as the top of the cusps of the teeth 8 or the bottom of their grooves. These common reference values permit the central unit 3 to combine the two files into a single one, while preserving their specificities.

Also, the use of a specific light 5 can facilitate the 3D reading of the teeth that have a very specular reflection. This invention is perfectly compatible with this kind of camera invented by Duret in 1970 (DDS thesis, 2nd cycle Lyon—France 1973). Thus, the specific light can be an active and structured projection such as projection of grids or other patterns. It is also possible to use cameras that do not use structured light, but based on the principles of passive stereoscopy (AWS or the like) or on the technique such as the time flight or holographic techniques or its derivatives such as OCT. This new device is fully universal and applicable to any form of viewing and/or intraoral localized measurements. Unlike the architectural techniques conventionally used by the augmented-reality glasses that search for specific points, it uses a dual optical impression, the one proceeding from the intraoral cameras 4 and the one performed at the same time or with a delay through augmented-reality glasses 1 in order to enrich them and/or to replace them depending on their degree of accuracy.

Likewise, it is possible to export the data in order to view them on a peripheral screen 7 for his assistants with whom he communicates by means of a microphone on the glasses or an independent microphone 11 or also to use them to carry out a machining 12 implant guides or anatomical parts during the work on the patient 13, which permits him to better understand the immediate environment during his working in the mouth. This machining can be done by subtraction (conventional machining by milling) or by addition (non-conventional machining such as laser melting or stereo lithography).

Figure 2:
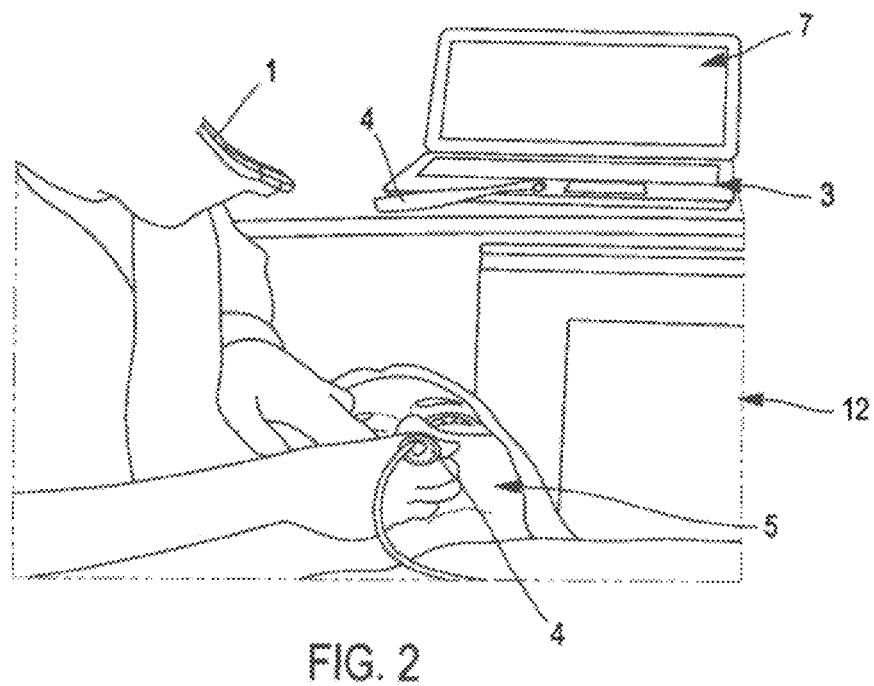
FIG. 2 is a schematic view of an overall representation of the partially made prototype including the camera, the connectors, the computer (here a laptop) and eventually a box containing the processing card.

FIG. 2 shows the invention in the form of a prototype, a part of which has already been made. In the case being presented is used an intraoral reading camera 4 in passive stereoscopy and with special lighting 5 for measuring the visible part of the mouth (teeth and gums). The central unit 3 is powerful and conventional, but the software is specific to the invention. The glasses used are the classic Google Glass 1, to which accelerometers and two cameras are attached. The machine tool 17 is a material-removing machine adapted by the inventor's laboratory.

Figure 3:
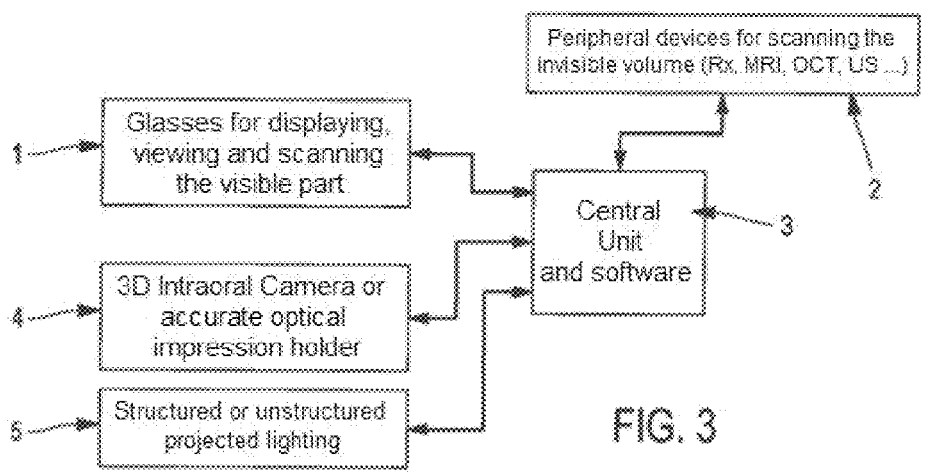
FIG. 3 represents a complete diagram of the essential elements of the device specific for the invention.

FIG. 3 is important, because it is the diagrammatic representation of the core of the device, object of the invention.

It shows augmented-reality viewing glasses 1 permitting the clinician to see the complemented object, i.e. his operating field visible with direct vision, but also the perfectly correlated and digitized visible and invisible parts in the form a single combined virtual object with direct vision. The peripheral devices 2 capable of transmitting the information about the invisible part of the mouth are connected or not directly to the central unit and make available this a priori information (RX . . . ) or real-time information (ultrasound . . . ). The central unit 3 permanently communicates with the glasses, so that the complemented object can be seen according to different angles. To this end, the software is based on the clouds of 3D point common to the view of the stored invisible part and the 3D view observed by the clinician via the cameras carried by the augmented-reality glasses.

The complemented object must therefore be regarded as a stable object in an orthonormal reference mark with respect to the cameras of the augmented-reality glasses. This object represents a sort of more or less cubic volume around which the observer turns. These are the common references or other added indexes (indexing wedges) that permit the clinician to turn around the virtual complemented object, as he would do with a hologram.

In order to make this matching of the two clouds of points reliable, it appears useful to make a more accurate recording of the visible surface than is the case with the cameras carried by the augmented-reality glasses. To this end is added an intraoral camera 4, which permits the accurate scanning of the visible surface, the camera using or not structured light, lighting, whether special or not, permitting an optimal view of the mouth, of the teeth and the gums.

Also, in order to provide a significant addition to the diagnostic aspect of the present invention, the device of the invention comprises a specific lighting 5 optimizing the reading of the hard dental tissues (white and blue light), but also permitting to highlight determined diseases of the hard tissues or the soft tissues (fluorescence, phosphorescence, reaction to IR radiation, mixed IR/near UV . . . ).

During the carrying out of these clinical actions, advantageously and according to an additional feature of the device according to the invention, indications 3 on the patient's physiological condition can appear in the operating field. It is indeed interesting to know the heart condition or other general information during particularly traumatic surgery.

FIG. 4 is a representation in images of steps of construction of the complemented 2-3D image. In a first step, the clinician takes a 2D, 2D½ or 3D view (FIG. 4*a*) thanks to the peripheral device 2. A 2D view (e.g. RVG), a 2D½ view (tomo, cone beam, OCT, or scanner) or better, a 3D view (MRI, ultrasound) permits to have information about the invisible structures. Like the roots 14 or crowns of the teeth 15, this information will be directed to the hard tissues in radiology or to the soft tissues in MRI, the cone beam being a good compromise between both. The clinician looks at his operating field in the mouth. The augmented-reality glasses carry stereoscopic cameras permitting to view the visible part of the mouth in 3D, i.e. the crowns of the teeth 16 and the surface of the gum 17 (FIG. 4*b*). He can also use an intraoral reading camera/scanner 4 if he wants to have a high accuracy in his reading of the visible part of the complemented image. This is the case for the image shown in FIG. 4*b*. The central unit will search the clouds 18 common to the first image of the invisible part (here radiological 4(*a*) and the second image of the visible part (here using our condor scanner 4*b*). It shows a common cloud of points (FIG. 4*c*). This cloud corresponds to the tooth crowns 19, since they are not deformable and present in both visible 16 and invisible 15 parts. From this common cloud of points, the software present in the central unit will bring the two structures together and combine them at the level of the cloud of points in order to form a single 3D volume object or complemented object 20 combining the visible 16 part and the invisible part. This object (FIG. 4*d*) will be displayed on the augmented-reality glasses. The dentist thus sees in the mouth of his patient the visible part and the invisible part, which permits him to treat not only the crowns, but also the tooth roots and the osseous structures of the maxilla.

Then remains for the software of the central unit 3 to follow the movements of the dentist's eyes in order to permit him to bypass this complemented object. To this end, the cameras located on the glasses will continue to follow the different orientations the cloud of points 18 takes with respect to the direction of the cameras, thus the eyes of the dentist. This will result into a permanent resetting of the complemented 3D virtual image displayed on the glasses of the practitioner 1 as an information additional to that he naturally observes on his clinical site. This resetting will occur permanently and as he moves his eyes.

While the previous view was a lingual view, the next view (4*e*) is a buccal view. The clinician has taken his eyes away and sees the teeth on another face. In this view, the buccal roots are short 21, because it has a more plunging view of same. The complemented object 20 comprised of the visible and the invisible part keeps to the movement of the eyes and permits to discover the other side of the 3D image. This is particularly interesting because it is possible to see the emergence of the mental hole 22 and the exit of the nerves and the blood vessels 23.

According to the same principle of the triple combination intraoral camera/RX/augmented-reality view, additional feature of the device according to the invention, it is possible to know even more accurately the nervous environment, veins, arteries and anatomical structures.

The dentist thus knows exactly where he must pinch to have a perfect anesthesia of the anterior region (incisor and canine). He can also see the osseous rim of the mandible 24, very important for implantology.

It is obvious that an occlusal view, without transparency effect for the neurovascular bundle, respects the visible surface, which remains dominant over the invisible surface (4f).

This invention permits to see the entire dental anatomy directly in the mouth, on the site of clinical action, without having to take the eyes away or to make subjective adjustments in order to know where these anatomical elements are located. The action becomes accurate and secure.

Figure 4A:
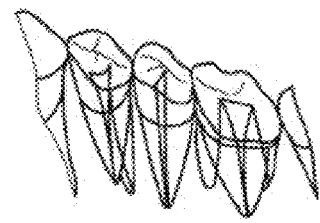
FIGS. 4A, 4B, 4C, 4D, 4E, 4F and 4G show schematic views of the various steps of correlation between the visible and invisible part permitting to create the complemented object based on their common areas, here the crowns of the teeth.
Figure 4B:
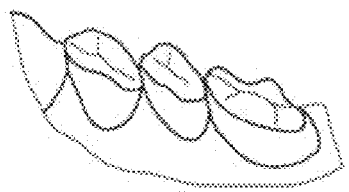
Figure 4C:
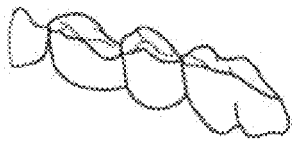
Figure 4D:
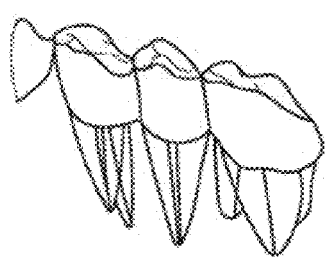
Figure 4E:
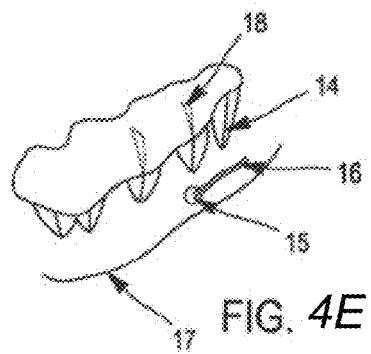
Figure 4F:
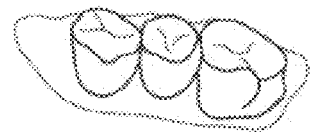
Figure 4G:
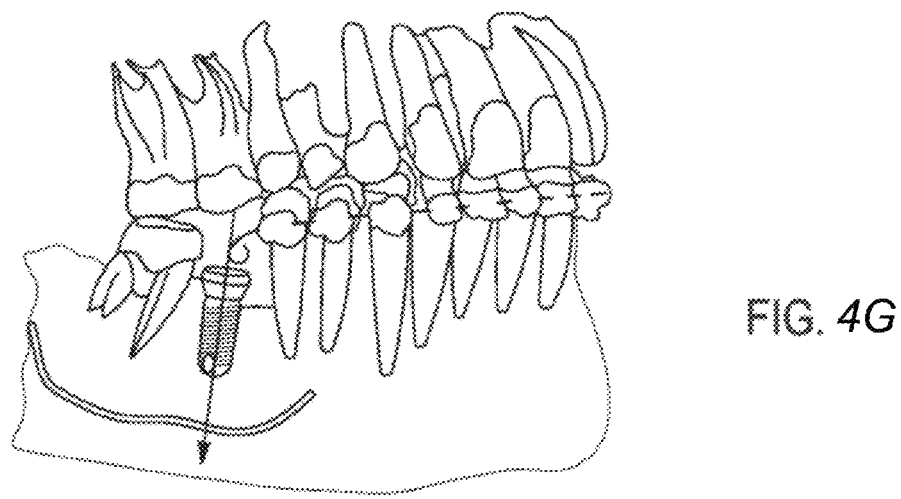

In FIG. 4g we see the view of the complemented object combining the visible and the invisible part into one set.

FIG. 5 illustrates the effect of the displacement of the clinician's eyes (5a) on the view observed through the augmented-reality glasses on the lingual (5b), occlusal (5c) or buccal (5d) view. When he moves his eyes, he is able to see inside the complemented object, normally invisible, either on the buccal view, or on the lingual view or on the occlusal view, which permits him to better understand the presence of important anatomical components, such as e.g. in FIG. 5d the emergence of the mental nerve 22.

FIG. 6 illustrates the effect of the change in the coefficient or index of transparency (known to the users of drawing software such as Photoshop).

Figure 6A:
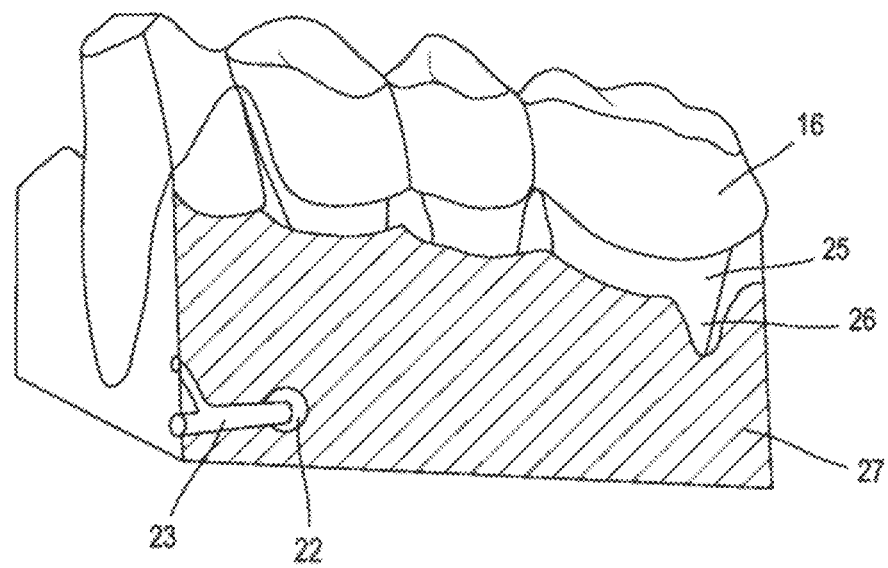
FIGS. 6A, 6B, 6C and 6D show schematic views of the various planes that can be observed by the clinician in the mouth of the complemented object when he uses the transparency function of the present invention.

In FIG. 6a, the gum is deleted on a plane closer to the observer, but the bone is visible. Visible are the crown of the tooth 16, the start of the root 25, the receding of the root 26 and the osseous surface 27. It is also possible to see the mental hole 22, which is so important for the anesthesia, and the emergence of the nerve 23.

Figure 6B:
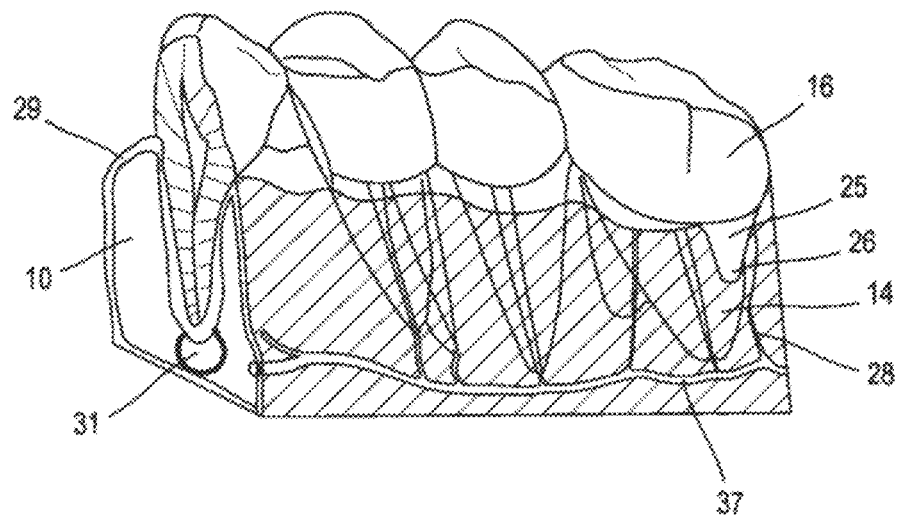

Visible in FIG. 6b, which is a deeper plane, are the crown 16, the start of the root 25 and its receding 26. In addition and by transparency in the bone are visible the root 14 and the nerve that reaches in the tooth 28. As shown in the segment at the left, the cortical bone 29 has been deleted in favor of the medullary bone 30, which also permits to see a cyst or a granuloma 31.

Figure 6C:
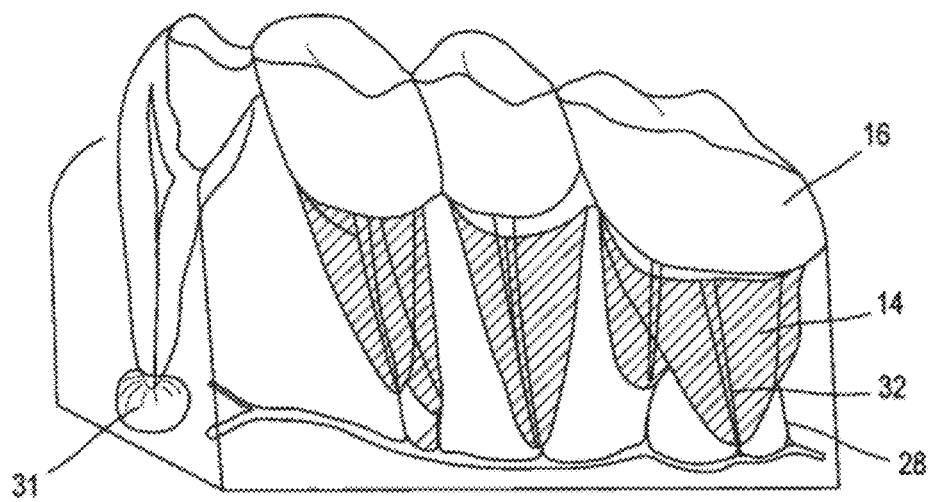
Figure 6D:
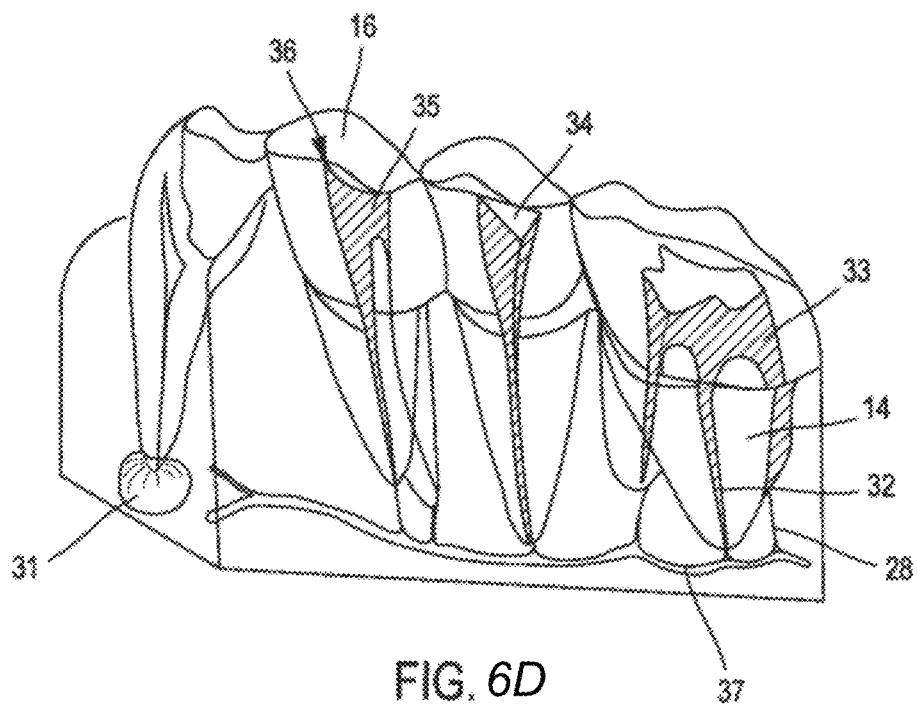

In FIG. 6c, where the medullary bone was made transparent, the clinician can see clearly in the mouth of his patient, in the extension of each crown 16, the root of the teeth 14, but also the nerve outside 28 and inside the tooth, the root canal 32 that contains it in the neurovascular bundle. The granuloma or the cyst are also more visible 31.

Finally, in the last plane selected in this example (which is non-restrictive) are clearly visible the coronary channel 32, here connected to the nerve and vessels external to the tooth 28, but also the coronal pulp of multi-rooted teeth 33 and single-rooted teeth 34, 35, which obviously permits to know perfectly the position of the pulp horns 36. Indeed, if the complemented 3D object is unique, it retains the knowledge of the visible and invisible part. The dentist will thus know exactly where he must open the tooth and penetrate into the root 36 to reach the nerve 37 with a minimum of decay for the tooth. This would also apply to the osseous structure if the clinician wanted to reach a granuloma 31, a cyst or a tumor. These different planes can be freely chosen with the foot, the keyboard or the path.

Figure 7:
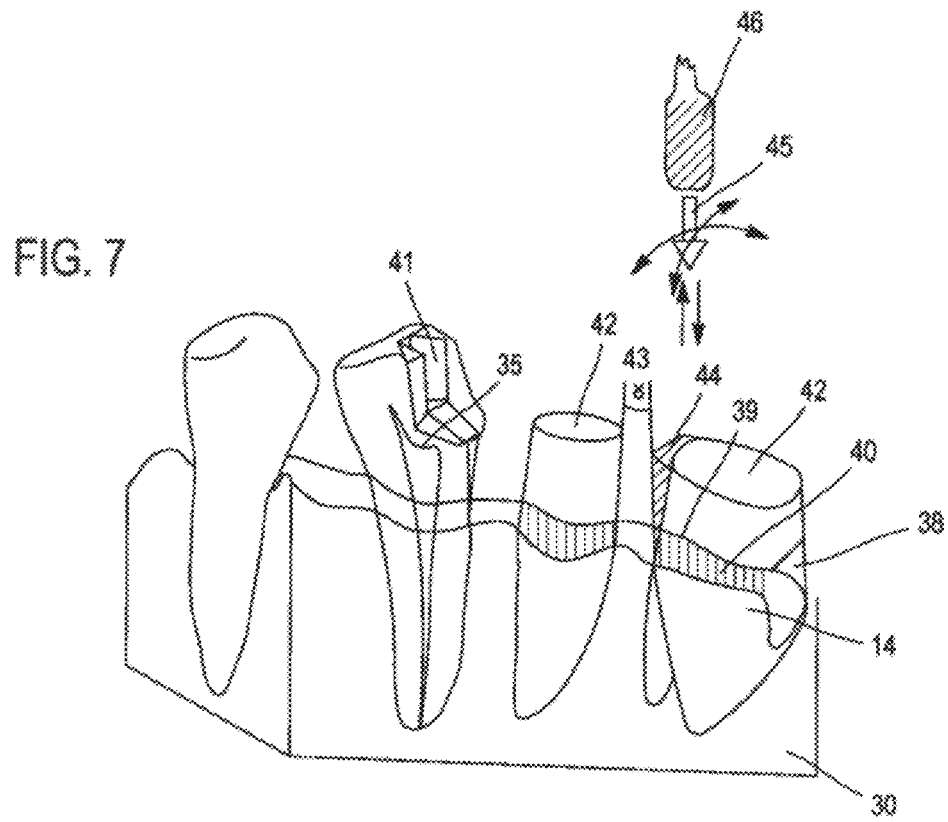
FIG. 7 represents the schematic view of the complemented object in the application of the present invention during the making of prosthetic preparations.
Figure 5C:
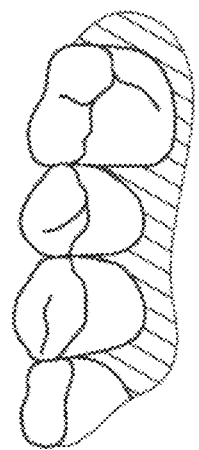
FIGS. 5A, 5B, 5C and 5D show various schematic views of a complemented object observed by the clinician in the mouth of his patient through augmented-reality glasses when he moves his eyes.
Figure 5A:
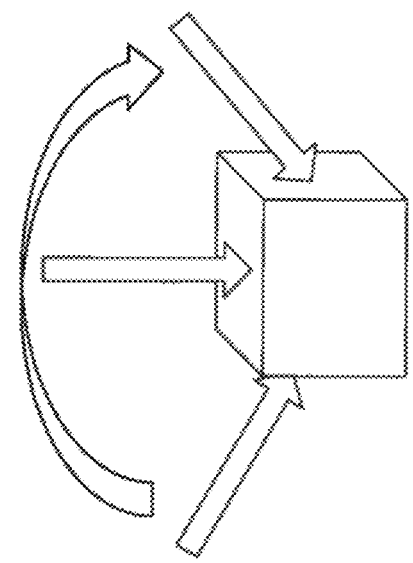
Figure 5D:
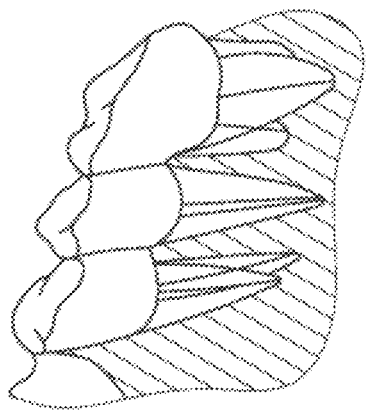
Figure 5B:
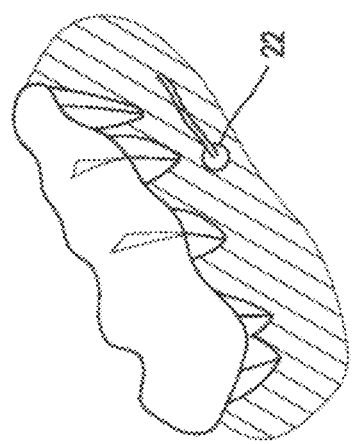

Also, more local information may be addressed to him. This can be, and this is non-restrictive, indications on the status of his work during or after its completion. For example, in FIG. 7 are indicated the undercuts 38 during a preparation of a dental prostheses or the fitting of an implant indicating what action and at what level has to be performed a correction or a modification of the work in order to ensure a proper prosthetic work. This indication appears in the form a color or texture overprint on the area to be worked on. It disappears when the work done meets the clinical need.

Also, shown in this figure is the form of the sub-gingival preparation invisible when it is covered by the gum. The supra-gingival part is visible directly in the mouth, the juxta-gingival part difficult to exploit by means of the direct methods, while in this invention it is clearly visible 38, as well as the sub-gingival part 40. This permits the clinician to know perfectly whether he must perform corrections. When he prepares an inlay/onlay 41, indications are given to him directly in the mouth in augmented reality on his preparation, which indications disappear when the preparation is carried out properly.

The same will apply to the making of a bridge. The calculation of the insertion axis 42 resulting from the analysis, for example, of the centers of gravity, will show him to maintain the angle to be formed 43, the area to be corrected 44, but also the angle 46 his drill should adopt when it is provided with a 3D spatial position sensor 45.

As illustrated in FIG. 8, the present invention permits to associate with the complemented object the dynamic monitoring of the tools used by the dentist or surgeon when performing an action of root treatment, surgical procedures such as an extraction of a tooth or also the fitting of an implant.

It is possible to monitor directly in the mouth and in real time, on the operating field and in the invisible part of the complemented object, without having to take his eyes away, his operating procedure and the movement of the instruments he uses in one and the same repository thanks to the augmented-reality glasses.

The clinician can monitor in time the displacements of cloud of points or the characteristic or stored modelings, which are thus known a priori, of his work tools in the mouth region.

Thus and advantageously and according to an additional feature of the device according to the invention, as we see in FIG. 8a, these instruments are handled as follows:

- The first step consists in locating in space the instrument being used, at the start of the operation, using the cameras 9 located on the augmented-reality glasses 1 and thanks to specific references 47 (e.g. a head of an instrument of a particular shape or with a bar code).
- The instrument being used is searched in a library containing a set of stored instrument shapes. In this case, the instruments are modeled by software based on their image with a particular identification making them easily identifiable. This may be a marker attached to the handle of the instrument or WiFi or magnetic message, without this being restrictive, the principle of the invention being a recognition of the object being used by the clinician.
- It is also possible to identify and to indicate manually its position on a screen. This has the advantage of facilitating the image-processing work, but obliges the practitioner to intervene on the attached screen.

The second step consists in monitoring the movement of this known instrument positioned in the space of the complemented object. This monitoring is possible, in real or almost real time, by the cameras 9 that tracks the movements of the points of the markers previously identified in the space by the image-processing software.

This monitoring is thus a dynamic matching in real time or with a slight delay of the instrument and the complemented object by monitoring these reference marks characteristic for the instrument being used and the characteristics non-deformable areas of the complemented object.

A sound or visual indication may be added if there exists a risk of reaching sensitive areas (veins or nerves . . . ).

A visual or sound indication can also be added for the clinician's procedure to be accurate and in the right direction (impacted teeth or granulomas, even cancer) with information permitting an ideal or even automatic orientation, or the appearance of a zoom to better view if there exists a risk.

The practitioner has thus a view of the displacement of these instruments in the complemented object as if he were using a dynamic radio. This is particularly interesting, because he can monitor the progress without any ionizing radiation.

Figure 8A:
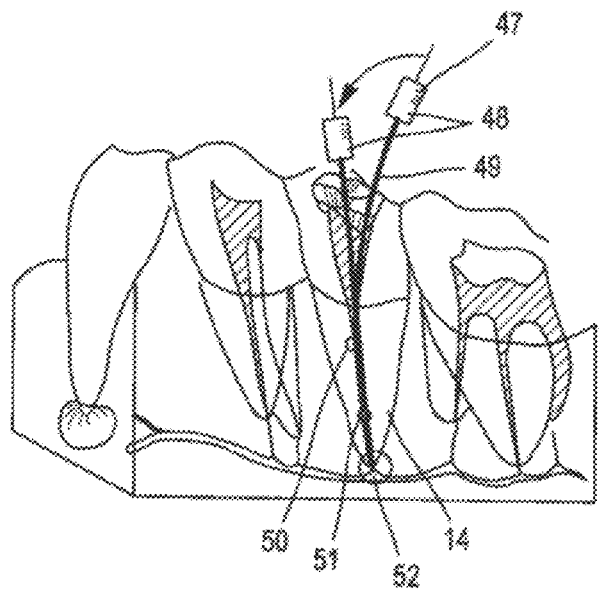
FIGS. 8A, 8B, and 8C show schematic views of the complemented object observed in the mouth by the practitioner when using a stored or recognizable instrument deformable for a root canal treatment or non-deformable for drilling an implant or a surgery operation.

As shown in FIG. 8a, the instrument being used is comprised, for example, but this is not restrictive, of two parts, a non-deformable one 48 containing the spatial identification elements 47, permitting to recognize and monitor the object in its movements in space, and another part corresponding to the active area 49, which is clinically efficient. These areas may be combined.

Thus and advantageously and according to an additional feature of the device according to the invention, there will be two possibilities.

Either the instrument is deformable, such as for example a spindle 48, a probe or a drill bit for the endodontic treatments. In this case, the instrument is correlated to the density, or in contrast, and this is given as an example only, the area in which it is inserted into the complementary object. This area of the same optical quality 50, in the 3D image (progression area) can be automatically identified or indicated by the operator. The instrument will deform so that it follows that this density or this contrast 51. For example, a deformable canal instrument will be inserted into a chamber 50, then a dental canal 51, which have a density, a very particular gray level with respect to the dentin of the root 14. This instrument, which the software has recognized and modeled, will deform to follow the characteristic density or the contrast of the canal.

Figure 8B:
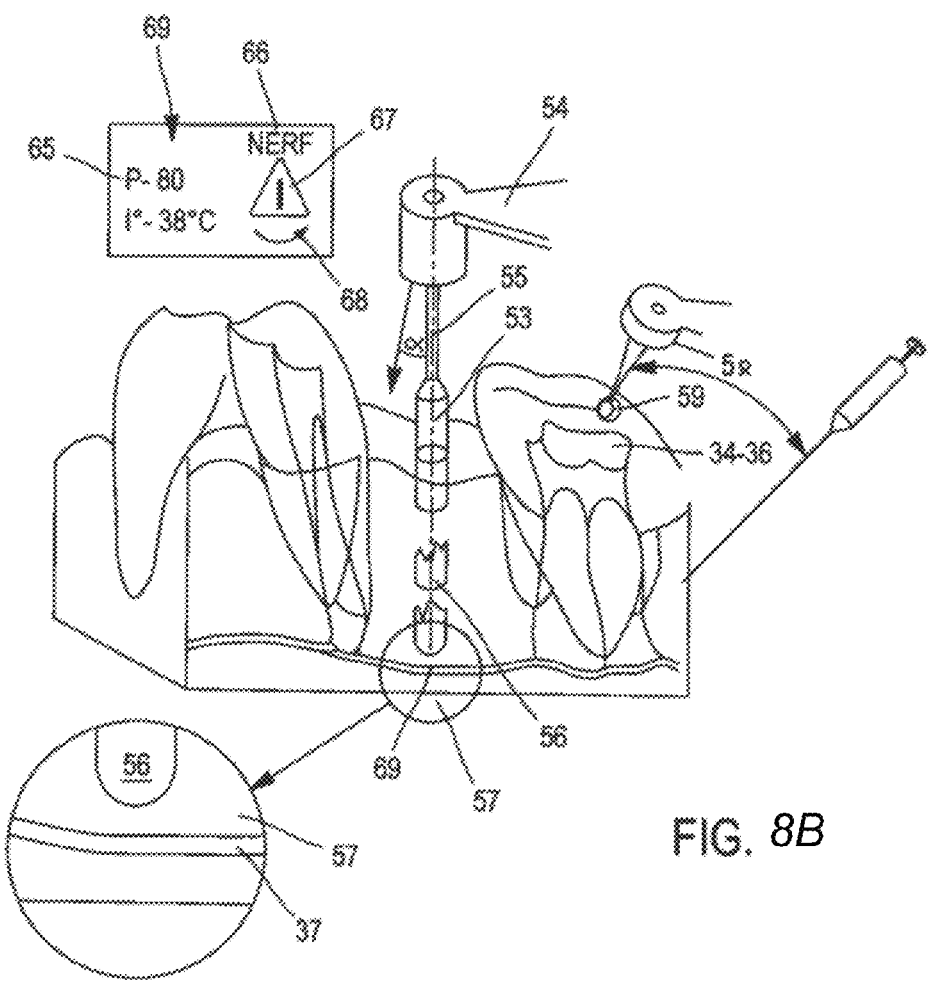

Or the instrument being used is non-deformable, such as for example in the FIG. 8b a drill 59 or a needle 58. It passes through the complemented object without taking into consideration the densities or contrasts characterizing different anatomical regions. The software is able to anticipate this instrumental movement and the risks of danger that comes with it (hitting a nerve or a vessel, even the risk of perforating a sinus in the upper jaw).

Thus and advantageously and according to an additional feature of the device according to the invention, the non-deformable or deformable instruments are stored in a specific library. This permits the clinician to select them manually or to launch an automatic search. The geometric characteristics of the instrument having been stored, its integration into the image containing the complementary object is particularly easy. This recognition can also occur automatically through reading the reference in various forms (bar code . . . ) This identification being done, this leads to an automatic knowledge of the geometric data of the instrument, its easier identification in the image viewed by the cameras 9 of the viewing glasses and the monitoring of its movements in complemented object.

Thus and advantageously and according to an additional feature of the device according to the invention, the monitoring of the movements of the deformable or non-deformable instrument will occur by optical means, but also by any technique for location in space (accelerometer, gyroscopes, magnetometers, ultrasound, IR, GPS . . . ).

As shown in FIG. 8b, in implantology it is possible to indicate the best position and the best insertion axis for the drill preparing the implant site. When the tool 54 is provided with a three-dimensional marking, for example such as the one of the French patent No. 92.08128, but this is not restrictive, the software indicates in augmented reality on the display glasses, directly at the level of the drill or the hand-operated part (at choice), the axis to be maintained 55 and emits a sound signal with varying tone depending on the accuracy or on the drift 68 of the position or the proximity of an anatomical element 66. The local information can also appear superimposed on the augmented-reality glasses 69 associated with the software present in the central unit 4. It shows all the information 69 in real time and guides to focus perfectly the drilling 65-68 and to stop it when it is deep enough 67. Also, and still in implantology, the invention indicates the type of implant, the shape or the brand that best meets the analyzed three-dimensional environment, thanks to the triple combination 9 viewed in augmented reality by the operator and it is necessary to manufacture the accurate picture/augmented-reality image/RX picture.

In some cases, no implant or no prosthesis corresponds to the ideal environment implant or prosthesis to measure. Advantageously and according to an additional feature of the device according to the invention, the central unit 3 is connected to a numerical-control machine tool 12 in order to manufacture this specific implant or prosthesis, in one or more units.

When the implant drill approach a hazardous area (here a nerve 37), it is possible to have (automatically or on request) an enlarged view of the risk area 57. This permits to better control the movement of the drill bit 56 relative to the nerve 37.

Figure 8C:
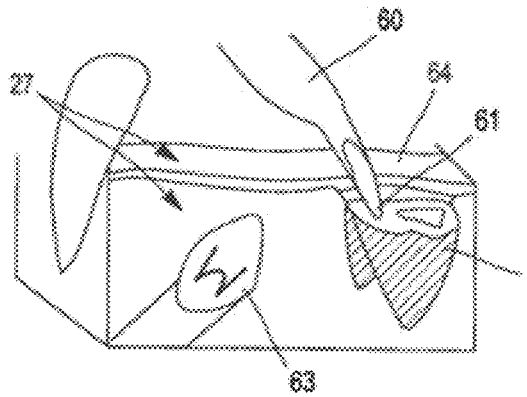

Finally, as can be seen in FIG. 8c, it is possible to monitor a surgery action in the complemented object. In the example shown, the non-deformable object 60 being used is a riser, permitting to arrive exactly at the root 62, which is normally invisible in the mouth. Thanks to the invention, it is possible to see it and to monitor in the complemented object the progression of the head 61 of the riser. The same applies to the search of an impacted tooth 63 located under the bone and the gum 27.

It is obvious that this application of the invention is not restricted to dentistry, but can be applied to any surgical operation on the body or in veterinary medicine.

Figure 9:
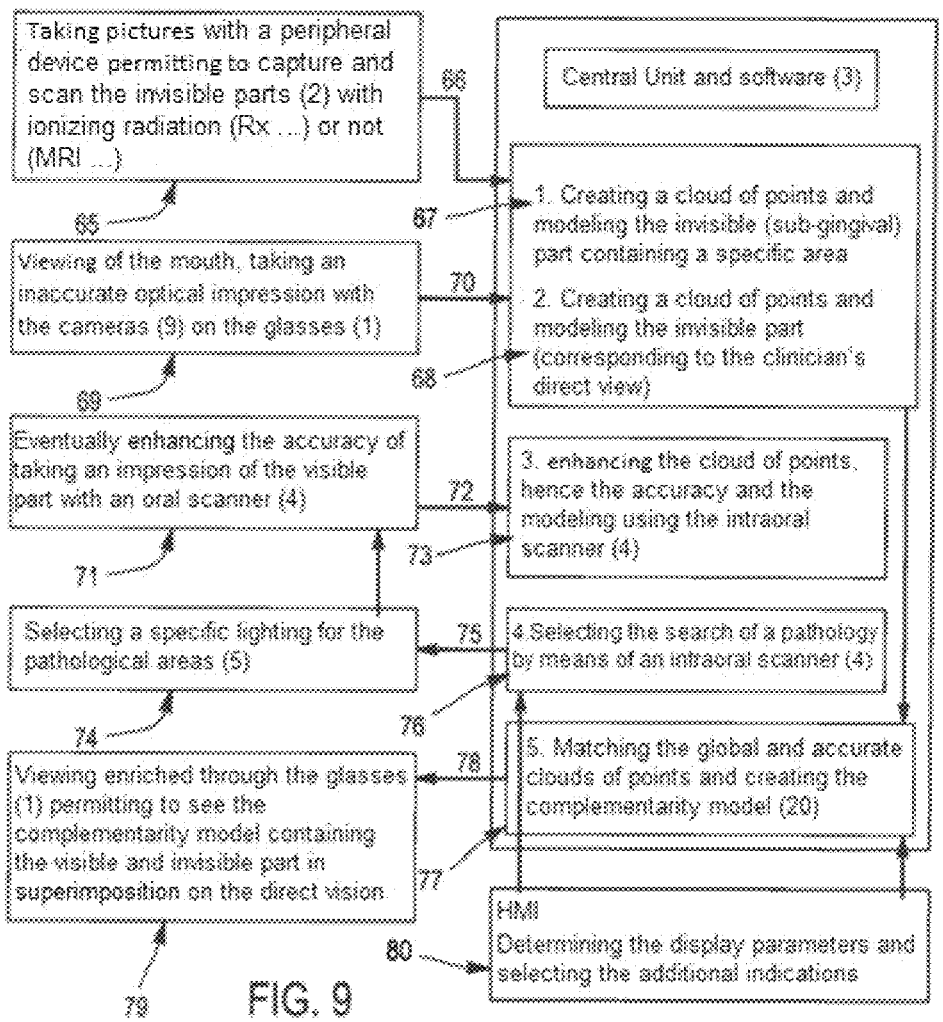
FIG. 9 is a diagram representing the various steps of the clinical manipulation permitting the implementation of the present invention.

FIG. 9 explains, through a diagram, the different clinical steps of manipulation.

The first step consists in recovering, from the peripheral device 2, the information of the invisible part, i.e. a 2D½ or 3D view of the underlying tissues 65. This view corresponds to a cloud of points (the voxels) representing the teeth (crowns 15, roots 14 and conduits of the pulp tissues), the medullary and cortical bone 24, the vessels and the nerves 23, but also the anatomical geography of its invisible components. A file containing these voxels in the form of a cloud of points 66 is sent to the central processing unit 3 in a file with as a support a STL, Ply . . . or Dat.com language (this is only an example, each language having a characteristic that is specific to it).

When the file of the invisible part 67 is received by the central unit, the practitioner can take his glasses 1 and view its working area in the mouth of his patient 8 and, using the HMI, turn on the augmented-reality glasses. This permits him to recover a second cloud of points 68 of the visible part in the mouth of his patient through the action of the external cameras or/and optical impressions 69 and their connections 70 to the central unit 3.

If he wants, the user can enhance the precision of his cloud of points using optical-impression cameras with or without structured light 71. This action permits to send and accurate cloud of points to the central unit 72, which will enhance the quality of the cloud 73 of the cameras on the augmented-reality glasses 68 relying on the areas common to the cloud of points of the complemented object and its visible parts 68 and invisible parts 67.

Using a specific lighting 74 of the intraoral camera, he can enrich the information 75 received by the central unit, mainly in the field of diagnosis 76.

At this stage, he will have two clouds of points 67, 68 reinforced with accurate information 73 and eventually diagnostic information 76. A combination then occurs at the level of the central unit 77 and creation of the complemented object. This object is then transmitted 78 to the augmented-reality glasses so that the complemented object is displayed in the field of viewing 78 and that the practitioner can see in the mouth of his patient the visible and invisible parts of his operating field 79.

All these orders are under the control of a specific manual or sound HMI 80.

The connection to the HMI and the practitioner's procedure is the freer and his vision is the more direct as the connection between these different units occurs by a long cable or wireless (Wifi, Bluetooth . . . ). The wireless connections are preferred, but this is not restrictive of the invention. If the connections are by cables, it is preferable to use, for example, a self-powered USB connection.

If the connection is wireless, it can be for example in WiFi mode, but this is not restrictive of the invention. In this case, if it is not originally present in the peripheral device, the antenna will be added in the camera 4, the augmented-reality glasses 1 and the other peripheral devices 2. Likewise, on the computer 3 or eventually on an intermediate casing will be inserted into the USB connection an antenna for sending and receiving data corresponding to the orders given by the dentist 6 using his microphone 11, by the program located in the computer 3 or the intermediate casing 3 if it does not have this transmission function. This arrangement will permit a fast, friendly and easy communication, irrespective of the configuration of the dental practices.

As can be seen in the diagram of FIG. 9, it is possible to send or receive other important information. This information can permit the clinician to work with comfort and accuracy. This is made possible through the creation of the complemented object and the viewing through augmented-reality glasses 1, without moving his eyes from the operating field 8.

Thus and advantageously and according to an additional feature of the device according to the invention, the practitioner will receive not only static information through combination and the creation of a complemented object 20, but also dynamic information by following the movements over time of the devices intervening on this complemented object. At any time will occur a resetting between the complemented object and displacements or variations imparted by the actions of the clinician 6 and viewed in augmented reality through his glasses 1.

All this mounting is achievable by following an accurate mathematical procedure. The accurate mathematical procedure can be the presentation of the software elements usable for the combination of both visible and invisible parts for creating the complemented object.

This is only one example of optical trace calculation by tracking points of interest. It permits to explain how to build a complemented object from the images received from the peripheral device 2 and the 2D ones from the reading using the cameras 9 on the augmented-reality glasses and/or those from the cameras for taking an optical impression 4.

The search for the optical traces of remarkable 3D points between the part common to the visible and invisible cloud occurs through searching points of interest in all the acquired images, then through searching matches between the points of interest of the different images.

Several schemes are possible:

A first scheme is the optical tracking of angles. The general idea is to calculate remarkable points (angles) in an image, then to track the points in the next images without having to re-detect them. The tracking phase continues as long as a determined percentage of remarkable points of the first image is still detectable (typically 70%); below this threshold, a new phase of detection of remarkable points is performed on the next picture.

The detection of angles occurs by calculating for any pixel (x, y) the matrix 2*2:

$$C = \begin{bmatrix} \sum w\left(\frac{\partial I}{\partial x}\right)^2 & \sum w\left(\frac{\partial I}{\partial x}\right)\cdot\left(\frac{\partial I}{\partial y}\right) \\ \sum w\left(\frac{\partial I}{\partial x}\right)\cdot\left(\frac{\partial I}{\partial y}\right) & \sum w\left(\frac{\partial I}{\partial y}\right)^2 \end{bmatrix}$$

wherein I designates the intensity at (x, y) of the picture and W a neighborhood of (x, y). Let $\lambda_1$ and $\lambda_2$ be the 2 eigenvalues of this matrix;

if these two values are above a determined threshold (typically 0.15), the point is considered as a remarkable point.

For the tracking is searched between 2 pictures i and i+1 and, for each remarkable point, the displacement $d=(d_x, d_y)$ which minimizes $$\Sigma w(I_i(x,y)-I_{i+1}(x+d_x,y+d_y))^2.$$

This displacement is calculated by $$'d = C^{-1}, b$$

with C the previously mentioned 2*2 matrix and $$b = \sum \begin{bmatrix} I_i(x, y) - I_{i+1}(x, y)\cdot I_i(x, y) \\ I_i(x, y) - I_{i+1}(x, y)\cdot I_{i+1}(x, y) \end{bmatrix}$$

Since this optical tracking technique is reliable for small displacements, the eventual large displacements are determined by sequentially calculating the displacement d over a pyramid of images (of a very subsampled version of the images until the original resolution).

The above-mentioned techniques are based on the implicit assumption that the image stream is consistent, i.e. the displacement between 2 successive images is small and 2 successive images are of sufficient quality to find a satisfactory amount of matching points (at least 30).

As regards the displacement between 2 images, the acquisition of the images occurs at a conventional video stream frequency. It is thus a very small displacement between 2 images. For a larger displacement, which would result into an impossibility to find matching points with the previous images, it will be possible to generate a new region.

As regards the insufficient quality of an image (in the event of a blurred image, for example), the matching phase acts as a filter, since it is clear that very few matching points will be found. The image will then be stored without being processed, and one will wait for the next image that will have a sufficient number of matching points.

A second scheme relates to the invariable points and the matching with the least squares.

The points of interest are sought in the pictures by well-known techniques, which search points remaining invariable through change of scale and illumination. These techniques have the advantage of being capable of calculating morphological descriptors for each point of interest.

The matching between points of interest for a given pair of images is performed by searching, for any point of interest $x_{11}$ of the image 1, the point of interest $x_{12}$ of the image 2 minimizing the distance with respect to $x_{11}$ to the least squares in terms of descriptors. In order to avoid the false matches or the outliers, the fundamental matrix F between the images 1 and 2 (which links the pairs of points of interest by the relationship $$x_{i1} \cdot F \cdot x_{i2}^t = 0$$

will be calculated in advance. If for a couple of points of interest $x_{11}$ and $x_{12}$ potentially matching the least squares, the product $$x_{i1} \cdot F \cdot x_{i2}^t$$

is higher than $10^{-5}$, then this pair is rejected.

The search for an optical trace then occurs by transition during the acquisition of a new image. When the image $I_j$ is acquired, it is assumed that the calculation of the optical trace has been performed for all the previous images $I_1 \ldots I_{j-1}$. Then are calculated the points of interest I; that are matched with the image $I_{j-1}$. Then are completed the optical traces by transition while noting that if $x_{ij}$ matches $x_{ij-1}$ and if $x_{ij-1}$ matches $x_{ij-2}$, then $x_{ij}$ matches $x_{ij-2}$.

A third scheme relates to the strong gradients and the matching by correlation.

As points of interest of an image are considered all the points where the intensity variations are important. In practice, for each point of the image being considered is calculated the standard deviation of the intensities close to 20*20 pixels around this point. If the standard deviation is above a determined threshold (typically in the order of 10, for intensities coded on 8 bits), the point is then considered as a point of interest.

The search for matches between 2 images at the level of their points of interest occurs by means of a correlation technique, for example, and this is not restrictive, such as the Medici (French patents filed on 29 Mar. 2005 EP1756771 (B0453) and EP0600128 (B0471)).

A real-time 3D reconstruction algorithm permits to monitor dynamically the movement of an instrument moving in the complemented object.

The 3D modeling follows three steps. In the first step, the 3D cloud of points obtained by processing optical traces is densified through the calculation of an implicit interpolation function f. Through this implicit function, the 3D surface interpolating the points is polygonized by the method, for example, and this is not restrictive, such as the Bloomenthal method. Finally, each polygon is textured in a very simple way: by projecting the 3D points delimiting the polygon in the images that generated these points, a polygonal area is delimited in these images. The texture on these polygonal areas is averaged and assigned to the polygon.

The main difficulty lies in the algorithm used for the interpolation and the calculation of the implicit function. This algorithm is optimally adapted to our use, because it permits an interpolation in real time and, unlike the other interpolation techniques, it permits dense interpolation from a very sparse initial cloud, which is very often the case when the work relates to objects with little texture, such as the teeth. We explain hereafter the generic interpolation underlying this algorithm, then its use in practice in a multiscale scheme.

Generic interpolation: Let Pi be the points of the 3D cloud (after estimating the normal $\vec{n}$ at these points), we will seek the implicit function f: $\mathbb{R}^3 \mathbb{R} \mathbb{R}$, based on Radial Basis Functions (RBF) such that the points x belonging to the surface are those for which f(x)=0. We choose f such that $$f(x) = \sum_{p_i \in p} [g_i(x) + \lambda_i] \cdot \Phi_\sigma(\|x - p_i\|), \text{ with}$$

$$\Phi_\sigma(x) = \Phi\left(\frac{x}{\sigma}\right), \phi(x) = (1 - r)^4 + (4r + 1)$$

The unknown values to be determined in order to explain f are therefore the $g_i$ and the $\lambda_i$.

Estimation of the $g_i$: Let's consider the point Pi and its normal $$\vec{n}_1$$

choose a system (u, v, w) such that u and v are perpendicular to the normal and w points in the direction of the normal. Let h be a function having the form $$h(u,v) = Au^2 + Buv + Cv^2,$$

in pi are searched the coefficients A, B and C so as the minimize the following quantity $$\Sigma_{P_j \in P} \Phi_\sigma(\|P_j - P_i\|) \cdot (w_j - h(u_j, v_j))^2.$$

Then gi (x) is calculated by $$g_i(x) = w - h(u,v).$$

Estimation of the $\lambda_i$: Knowing that $$f(P_i) = 0 \forall P_i,$$

we can estimate the $\lambda_i$ by a simple linear system resolution.

Multiscale interpolation: The generic interpolation is in fact performed on subsets of points in order to greatly improve the accuracy of the interpolation. First, a set $$\{\mathcal{P}_0, \ldots, \mathcal{P}_k\}$$

is constructed as follows: The set $\mathcal{P}_0$ is a parallelepiped comprising all the points Pi. Between 2 successive levels k−1 and k is carried out a subdivision of parallelepipeds into 8 small parallelepipeds.

The function f is calculated by an iterative procedure. We start from $$f^0 = -1,$$

then we iterate over the sets $\mathcal{F}_k$ while updating f:

$$f^k(x) = f^{k-1}(x) + o^k(x), \; o^k(x) = \sum_{p_i^k \in p_k} (g_i^k(x) + \lambda_i^k) \cdot \Phi_{\sigma^k}(\|x - p_i^k\|)$$

The $g_i^k$ are determined as described above over the set $\mathcal{F}_k$ and the $\lambda_i$ are calculated by solving the system $$f^{k-1}(P_i^k) + o^k(P_i^k) = 0$$

The $\sigma^k$ are updated such that $\sigma^{i+1} = \sigma^k/2$, and the number of levels to be built is defined by $$M = -\log_2(\sigma^0/2\sigma^1)$$

The manipulation of such a system is extremely simple, because its parameterization is deemed fixed and unchangeable by the operator, except for determined pre-manipulation and other (preset) selections requiring precisions during the work. In the first one can be found for example the patient's file (clinical file), while in the other one can be found the instruments he can use (whether deformable or not), the selection of the kind of viewing (e.g. with or without the bone) or also the type of diagnosis aimed at (e.g. caries or tumors, which will not have the same type of lighting).

This function can be controlled by a series of automatic actions leading to the desired diagnosis. To this end, the operator (dentist, dental technician or physician) has a computer indicating the operations that the augmented-reality glasses and/or cameras (whether augmented or not with an accurate reading with the intraoral scanner), asking him to make the choice between one feature and another.

It should be noted that the clinical actions are privileged over the type of material. So, we do not mention on scrolling menu or in voice detection fluorescent light, but caries detection.

All or part of the treatment can be performed at the level of the maps included in a generic system (standard laptop or desktop) or in a specific system including cards specially dedicated to the application of data-processing, transmission and display. This set may be integrated into the Unit or separated (e.g., in a kart).

The first step consists in collecting the 2D, 2D½ or 3D invisible images from the peripheral device 2 and in storing them delayed (RX, IR, MRI . . . ) or in almost real time (ultrasound, OCT . . . ). When the practitioner observes that the storage is done, he is ready to launch the construction of the complemented 3D or pseudo 3D object.

The second step consists in taking his augmented-reality glasses 1 and in launching the reading by the cameras 9. The actual image seen through the glasses is successively enriched:

First of all, with the 3D modeling of the visible part built with the two cameras 9 fixed on the glasses 1. Although this is possible, for safety reasons, there is never elimination of the direct view in favor of the modeled representation in the field of view, but a combination between the direct view and this modeling resulting from the cloud of points (see the Duret and Coll. Patent BV 4).

Then the clinician retrieves the view of the invisible part from the selected peripheral device 2, which, based on the common points, will complement the modeled view of the two cameras 9, in order to create the complemented object containing the visible part and the invisible part.

If the clinician wants to have a perfect view with good definition of the visible view, he has the possibility of performing an additional scanning using an intraoral optical reading camera 4.

Eventually and in order to facilitate the combination of the two clouds of points, those from the reading performed on the invisible part 2 and those from the reading of the visible part by the glasses 1 and 9 and the intraoral scanner 4, he can indicate using a specific instrument the area common to both files (for example the crowns of the teeth) directly on the site or on a nearby screen.

He can also use a calibration wedge permitting to homogenize the two views in terms of dimensions, thanks to the multi-scale interpolation software. Indeed, in some cases, in particular when the 2D view(s) has or have to be correlated on 3D cloud of points of the visible view, the match is more difficult. Based on the repository added in the invisible 2D view, this wedge easier permits the work of this software. Advantageously, and according to the invention, the LEDs can also play an important role in the correlation of the successive views. Indeed, we know that there are methods that base the correlations of the views on marks placed in the environment being measured or using the similarity found in the cloud itself, or even working on the fuzzy edges of the views. All these systems are complex, because they oblige either to place spherical marks in the area, which operation is clinically complex, or to identify areas often without relief or with a too smooth surface condition. Scanning with LEDs of known wavelength with 3D color imaging permits to simplify and to automate this procedure. Indeed, a simple colored line or gluing of a mark can be identified and displayed automatically if we took care to use a marking or identification using a complementary, identical color additive or subtractive of the wavelength of one (or several) of the scanning LEDs. The identification will thus occur by simply enhancing in color the mark, irrespective of its nature. This identification, which is always in one and the same position on the object, irrespective of the angle or zoom of our optical impressions, will serve as a correlation reference.

The combination function for the complemented object can be initiated using a button located on his glasses or close to his clinical seat, an oral information by means of the microphone 11 or a pedal in communication with the computer, and he can stop it when he judges that it is correct or that he has completed his clinical action. To this end, he stops pressing or presses a second time.

The cameras on the glasses will permanently interpolate the invisible file on the visible file, providing a full view of the supra- and sub-gingival part to the clinician's view directly in the mouth and in real or almost real time.

It should be noted that this visible/invisible combination operation can occur on a plaster model in a laboratory, whereby the technician may have augmented-reality glasses. This permits the technician to have interesting information when he has to prepare sub-gingival prosthesis, removable appliances that require knowledge of the thicknesses of the gingival tissues and osseous relief, surgical guides and prefabricated implants or implants made at measure in implantology through viewing, instead of the plaster, underlying organs (arteries, sub-gingival finishing line . . . ). Without this invention, the operation would be impossible.

The software processing permits to calculate in almost real time the 3D coordinates (x, y, z) and the color of each of the points being measured in x, y and z. We obtain a 3D file of a partial or full arch in color associated with information of the invisible part.

The taking of successive images with the cameras located on the glasses 1, real film of the zone to be viewed, permits a complete record of the information necessary for the digital processing of the whole or part of the object to be seen, but also to measure in buccal, lingual and proximal view if he wishes to use the stereoscopic measuring function that can be provided by a camera creating clouds of points (see Duret and Patent Coll. Patent FR 14.54774). These areas are combined automatically by the software with the inaccurate previous views based on the same common repertory (for example the crowns of the teeth). This same detection of the common areas can be performed at the level of the modeling curves (Nurbs, radial basis functions, wavelets . . . ).

If the practitioner decides to use the diagnosis function, he selects on the computer or orally the desired type of diagnosis, for example melanoma or caries detection, the camera will launch a scan of wavelengths corresponding to the highlighting of areas of interest for the preselected wavelengths present in a 3D image. In addition and through the 3D analysis of the object, the overlapping of the measurements over time will permit to better monitor the evolution of said pathology. It is indeed admitted by the professionals that the examination of a suspicious image may occur in 2D, but especially the evolution of its volume and its color serves as a reference for monitoring over time its dangerous nature. Having a volume referred to a mathematical center (such as the center of gravity) permits to superimpose the images on a center depending on the object and not on the observer, in order to objectively appreciate the evolution of its volume, the color analysis being carried over onto a 3D form, which is not the case today with the methods implemented on 2D surfaces or those using lights or structured waves (OCT, CT or MRI).

Likewise, by selecting determined wavelengths emitted by the LEDs present around the reading window and by increasing their frequencies and/or their intensities, we can carry over onto a 3D image viewing determined anatomies and pathologies located at any depth, in addition to those viewed by the peripheral device viewing the invisible part. The knowledge of the volume provides us with an indication of the positioning of this pathological limit, which permits us to predict and to view the evolution. This applies to the fluorescence reactions of determined tissues to blue or UV radiation. The fluorescence appears not only on the surface, but also in the depth of the pathology, which permits us to provide assistance to the therapy to be applied (removal of pathological tissues). Knowing the penetration of a particular radiation, we can appreciate its importance and depth relative to the 3D real surface being analyzed.

From the above description clearly appears that the present invention perfectly solves the problems raised in that it provides a real answer for the viewing of the visible and invisible areas and in particular their combining into one and the same repository permitting to view the complemented object directly in the mouth on the clinical site. It permits an immediate anatomical and pathological analysis of the diseases of the gums and the underlying tissues. From this description also clearly appears that it permits to solve the fundamental problems, such as the control of the clinical action, the more that no alternative method has been provided. It is obvious that the invention is not restricted to the only implementation of this method, nor to the only forms of carrying out of the device for implementing this method, given above as an example. Instead, it encompasses all the variants of implementation and carrying out.

Thus, it is namely possible to measure the oral diseases, whether they relate to the hard tissues and the soft tissues.

As we understand, we provide a universal device for viewing and measuring the visible and invisible parts during the clinical action taken in its field of application, meeting the many demands in terms of cost, ease of use, assistance for measuring and diagnostic imaging in dentistry.

This system can be applied for example in a progressive form to any 3D acquisition requiring a fast and accurate manipulation obliging the operator not to take his eyes away from his field of work, analysis and/or measurement. This is the case for the works performed on all parts of the human body, the data acquisition requiring not be disturbed by sudden movements of the patient, the quick action such as sports actions or the industrial production procedures, in particular in a hostile environment. It is thus possible to monitor and inform the operator in real or almost real time, while permitting him not to take his eyes away from the scene and displaying additional information.

From the above description clearly appears that the present invention perfectly meets the problems raised, in that it provides a real answer for the viewing of the visible and invisible areas and in particular their combining into one and the same repository permitting to view the complemented object directly in the mouth on the clinical site. It permits an immediate anatomical and pathological analysis of the diseases of the gums and the underlying tissues. From this description also clearly appears that it permits to solve the fundamental problems, such as the control of the clinical action, the more that no alternative method has been provided. It is obvious that the invention is not restricted to the only implementation of this method, nor to the only forms of carrying out of the device for implementing this method, given above as an example. Instead, it encompasses all the variants of implementation and carrying out. Thus, it is namely possible to measure the oral diseases, whether they relate to the hard tissues and the soft tissues.

The invention can be used to perform any medical or nursing actions: it is possible for the viewing device to help in locating anatomical elements for a subcutaneous injection, an intravenous injection or the placing of a catheter; it is also possible for same to help in the study of the skin and gum thicknesses between the bone and the surface of the skin or the gum.

I claim:

1. A viewing device for an inside of a patient's mouth, the mouth having an organ, said viewing device comprising:
   a penetrating ray emitter having an anatomical view;
   a pair of augmented-reality glasses being comprised of:
      an optical glass having a direct view; and
      a viewing camera having an image view, according to position of said optical glass; and
   a central unit being in communication with said optical glass, said optical glass having a projected view, said projected view being comprised of said anatomical view, said direct view, and said image view, said anatomical view being visible through said optical glass over said direct view and said image view.

2. The viewing device according to claim 1, further comprising:
   a medical treatment instrument being positioned within said direct view and said image view; and
   a reference mark spatially identified in said anatomical view, wherein said projected view of said central unit is comprised of said medical treatment instrument and said reference mark, said projected view showing dimensions of said medical treatment instrument and distance separating said reference mark and medical treatment instrument.

3. The viewing device, according to claim 2, wherein displacement of said medical treatment instrument is equal to displacement of said reference mark, said projected view of said central unit being comprised of direction and movement of said medical treatment instrument, said direction and movement of said reference mark matching said medical treatment instrument.

4. The viewing device, according to claim 2, wherein said projected view of said central unit is comprised of a movement path of said medical treatment instrument.

5. The viewing device, according to claim 4, wherein said medical treatment instrument is guided by said movement path according to said projected view.

6. The viewing device, according to claim 4, further comprising: a sound emitter having a sound signal corresponding to said medical treatment instrument in position along said movement path in said projected view.

7. The viewing device, according to claim 2, wherein said medical treatment instrument is comprised of an identifier, and wherein said projected view of said central unit is comprised of said identifier.

8. The viewing device, according to claim 7, further comprising: additional treatment instruments, and a library of identifiers, each identifier corresponding to an additional treatment instrument, said projected view of said central unit being comprised of at least one identifier.

9. The viewing device according to claim 1, further comprising:
an intraoral camera having an intraoral view, said projected view of said central unit being further comprised of said intraoral view.

10. The viewing device according to claim 1, wherein said penetrating ray emitter is in wireless communication with said central unit.

11. The viewing device according to claim 1, further comprising:
a scanning device having a scan view, corresponding to said anatomical view of said penetrating ray emitter, said projected view of said central unit being comprised of said scan view.

12. The viewing device according to claim 1, wherein said projected view of said central unit is is further comprised of additional information, said additional information being comprised of data for a dental prosthesis.

13. The viewing device according to claim 12, further comprising:
at least one peripheral instrument connected to said central unit, said at least one peripheral instrument providing said additional information.

14. The viewing device according to claim 1, further comprising:
a microphone in wireless communication with said central unit, said microphone having control commands corresponding to said central unit.

15. The viewing device, according to claim 1, wherein the pair of augmented-reality glasses comprises a spatial marking instrument.

16. The viewing device according to claim 1, further comprising:
a lighting system connected to said central unit and generating light, said direct view being comprised of said light, said image view being comprised of said light.

17. The viewing device, according to claim 16, wherein said lighting system comprises light-emitting diodes.

* * * * *